United States Patent
Buolamwini et al.

(10) Patent No.: US 8,329,723 B2
(45) Date of Patent: Dec. 11, 2012

(54) 1-ARYL- OR 1-HETEROARYL-PYRIDO[B]INDOLES AND USES THEREOF IN TREATING CANCERS

(76) Inventors: John K Buolamwini, Cordova, TN (US); Shrivaputra Patil, Memphis, TN (US); Sharma Horrick, Memphis, TN (US); James K Addo, Kansas City, MO (US)

( * ) Notice: Subject to any disclaimer, the term of this patent is extended or adjusted under 35 U.S.C. 154(b) by 0 days.

(21) Appl. No.: 12/799,485

(22) Filed: Apr. 26, 2010

(65) Prior Publication Data
US 2010/0317667 A1 Dec. 16, 2010

Related U.S. Application Data

(60) Provisional application No. 61/214,582, filed on Apr. 24, 2009.

(51) Int. Cl.
*A61K 31/44* (2006.01)
(52) U.S. Cl. ........ 514/292; 544/353; 546/144; 546/167; 549/505; 585/26
(58) Field of Classification Search .................. 514/292; 544/353; 546/144, 167; 549/505; 585/26
See application file for complete search history.

(56) References Cited

U.S. PATENT DOCUMENTS

| | | | |
|---|---|---|---|
| 6,030,983 A | 2/2000 | Behforouz | 514/292 |
| 2006/0079497 A1 | 4/2006 | Behforouz | 514/210 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Kulkarni, et al. Tetrahedron Letters, 50(16), 2009, 1791-1794.*
Ho, et al. Canadian Journal of Chemistry, 45(23), 1967, 2963-2967.*
Mokrosz, et al. Mild Oxidation of 1,2,3,4-Tetrahydor-β-carbolines; *Polish Journal of Chemistry*, 1995, vol. 69, No. 2, pp. 264-268.
Hu, et al. Carboline Alkaloids from *Trigonostemon lii*; *Planta Med.*, 2009, vol. 75, pp. 1157-1161.
Li, Y. et al. DH334, a β-Carboline Anti-Cancer Drug, Inhibits the CDK Activity of Budding Yeast: *Cancer Biology & Therapy*, 2007, vol. 6, No. 8, pp. e1-e7.
Fang Y. et al. Characterization of the Cytoxic Activities of Novel Analogues of the Antitumor Agent, Lavendamycin[1]: *Molecular Cancer Therapy*, Jun. 1, 2003, vol. 2, pp. 517-526.
Hassani, M. et al. Novel Lavendamycin Analogues as Antitumor Agents: Synthesis, in Vitro Cytotoxicity, Structure-Metabolism, and Computational Molecular Modeling Studies with NAD(P)H:Quinone Oxidoreductase 1: *Journal Medicinal Chemistry*, 2005, vol. 48, pp. 7733-7749.
Formagio, A.S.N. et al. Synthesis and Antitumoral Activity of Novel 3-(2-Substituted-1,3,4-Oxadiazol-5-yl) and 3-(5-Substituted-1,2,4-Triazol-3-yl) β-Carboline Derivatives: *Bioorganic & Medicinal Chemistry*, 2008, vol. 16, pp. 9660-9667.

* cited by examiner

*Primary Examiner* — Douglas M Willis
(74) *Attorney, Agent, or Firm* — Benjamin Aaron Adler

(57) ABSTRACT

Provided herein are 1-aryl or 1-heteroaryl pyrido[b]indoles compounds with the structure

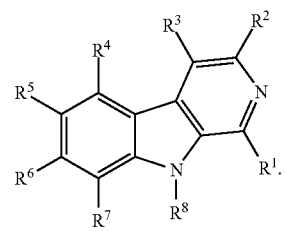

These compounds comprise a β-carboline ring structure substituted at C1 with an aryl or heteroaryl moiety and individually substituted at C3-C8 and N9 with a $C_1$-$C_4$ alkyl, a $C_1$-$C_4$ alkoxy, a $C_1$-$C_4$ alkoxyphenyl, or a hydrogen. Also provided are methods for inhibiting proliferation of cancer cells or for treating a cell proliferative disease by contacting the cancer cell or tumor comprising the same with the compounds provided herein or by administering the compounds to a subject with a cell proliferative disease.

7 Claims, 11 Drawing Sheets

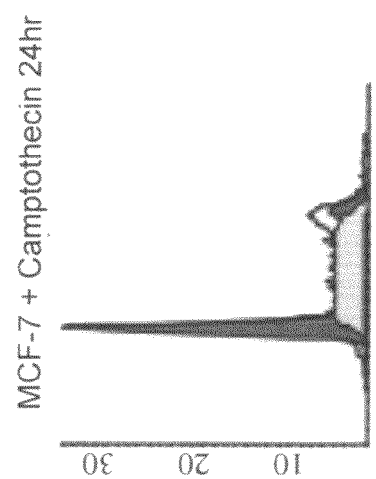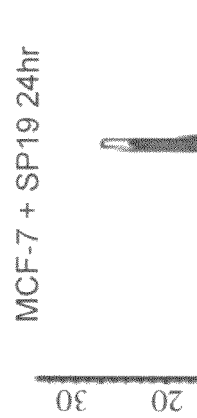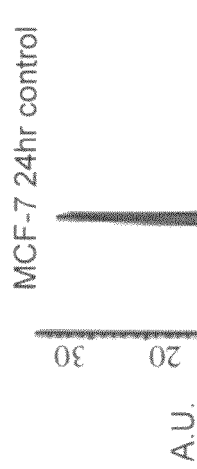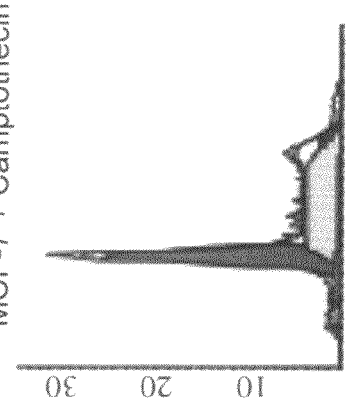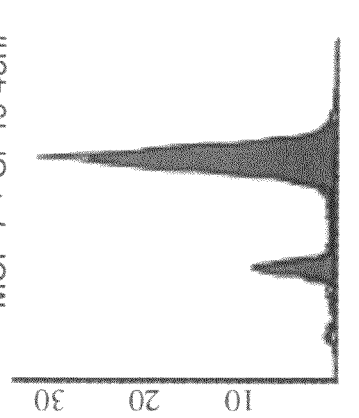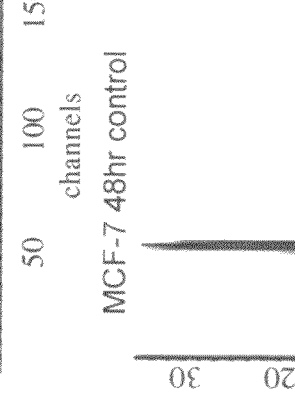
Fig. 4A  MCF-7 24hr control
Fig. 4B  MCF-7 + SP19 24hr
Fig. 4C  MCF-7 + Camptothecin 24hr
Fig. 4D  MCF-7 48hr control
Fig. 4E  MCF-7 + SP19 48hr
Fig. 4F  MCF-7 + Camptothecin 48hr

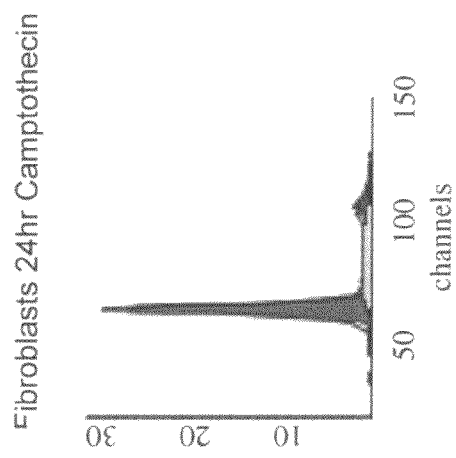
Fig. 5A Fibroblasts 24hr control
Fig. 5B Fibroblasts 24hr SP19
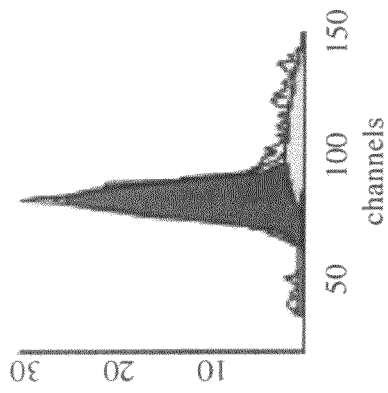
Fig. 5C Fibroblasts 24hr Camptothecin
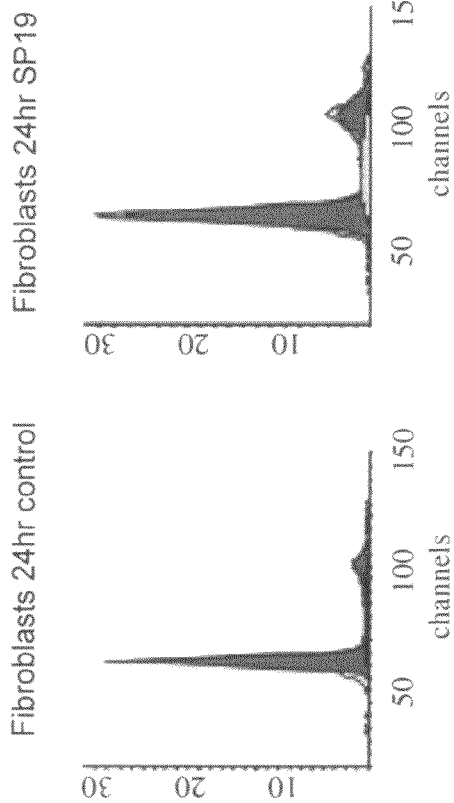
Fig. 5D Fibroblasts 72hr control
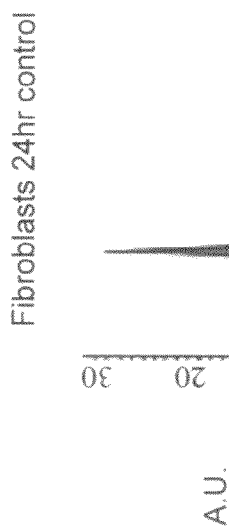
Fig. 5E Fibroblasts 72hr SP19
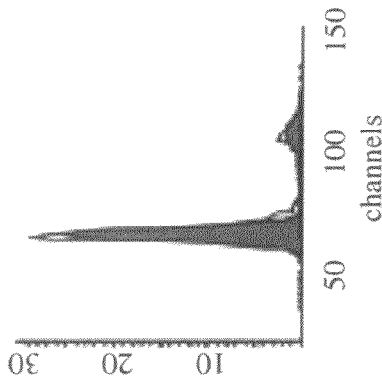
Fig. 5F Fibroblasts 72hr Camptothecin
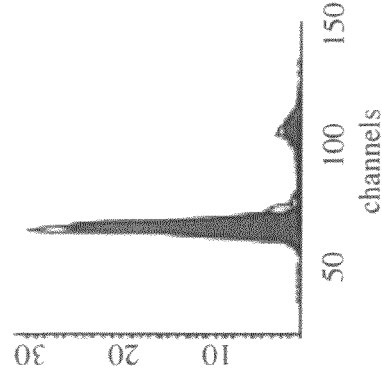

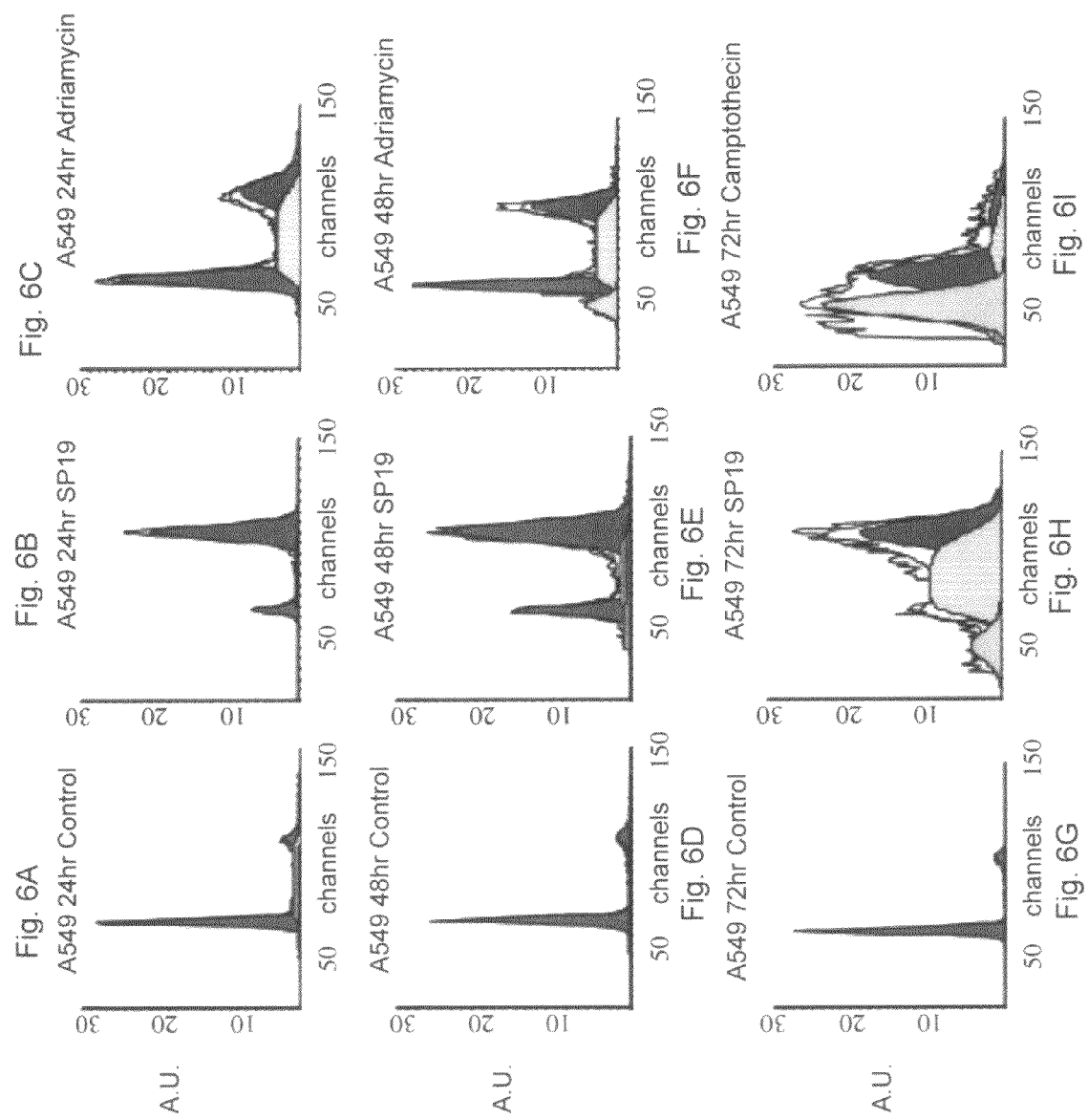

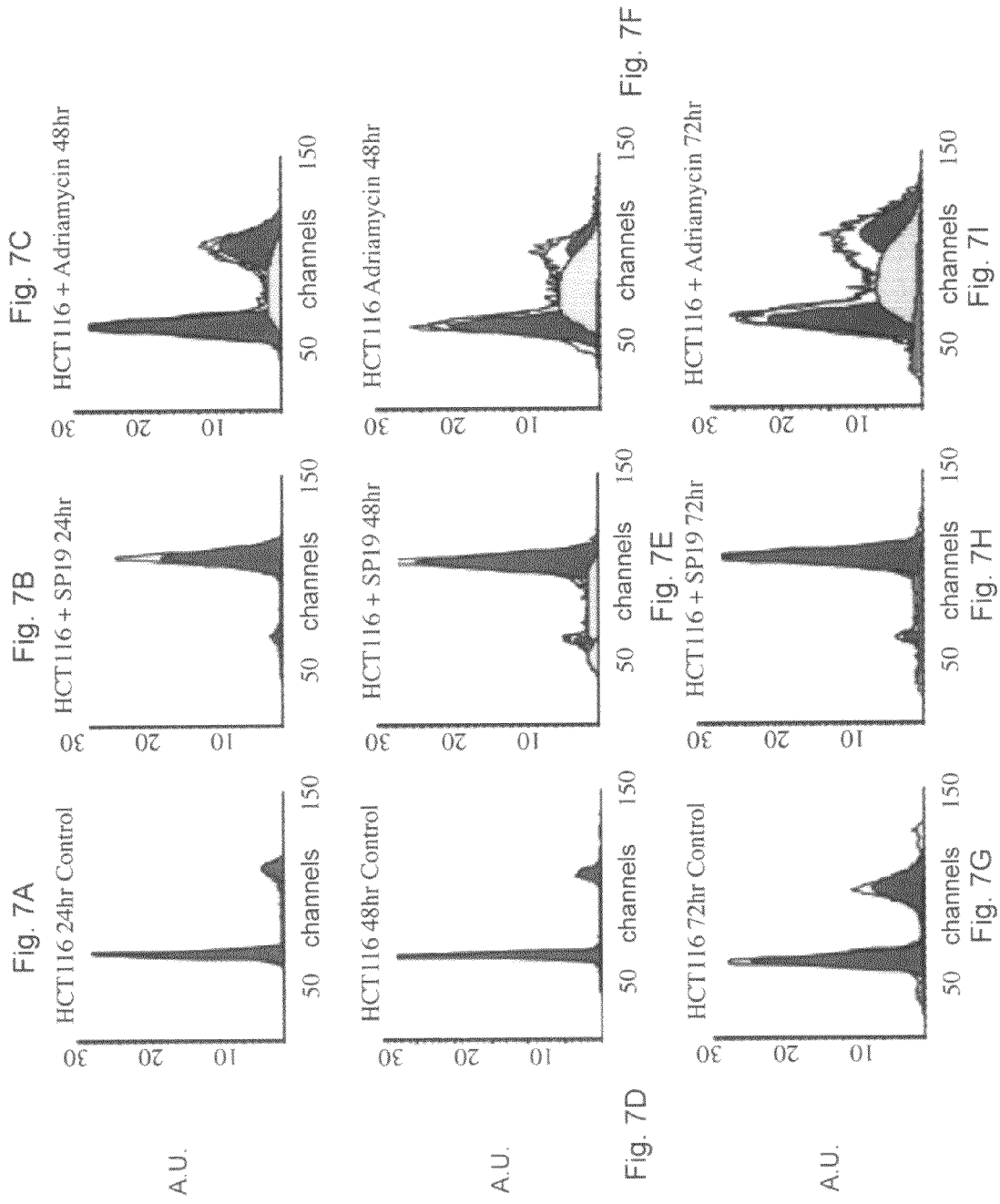

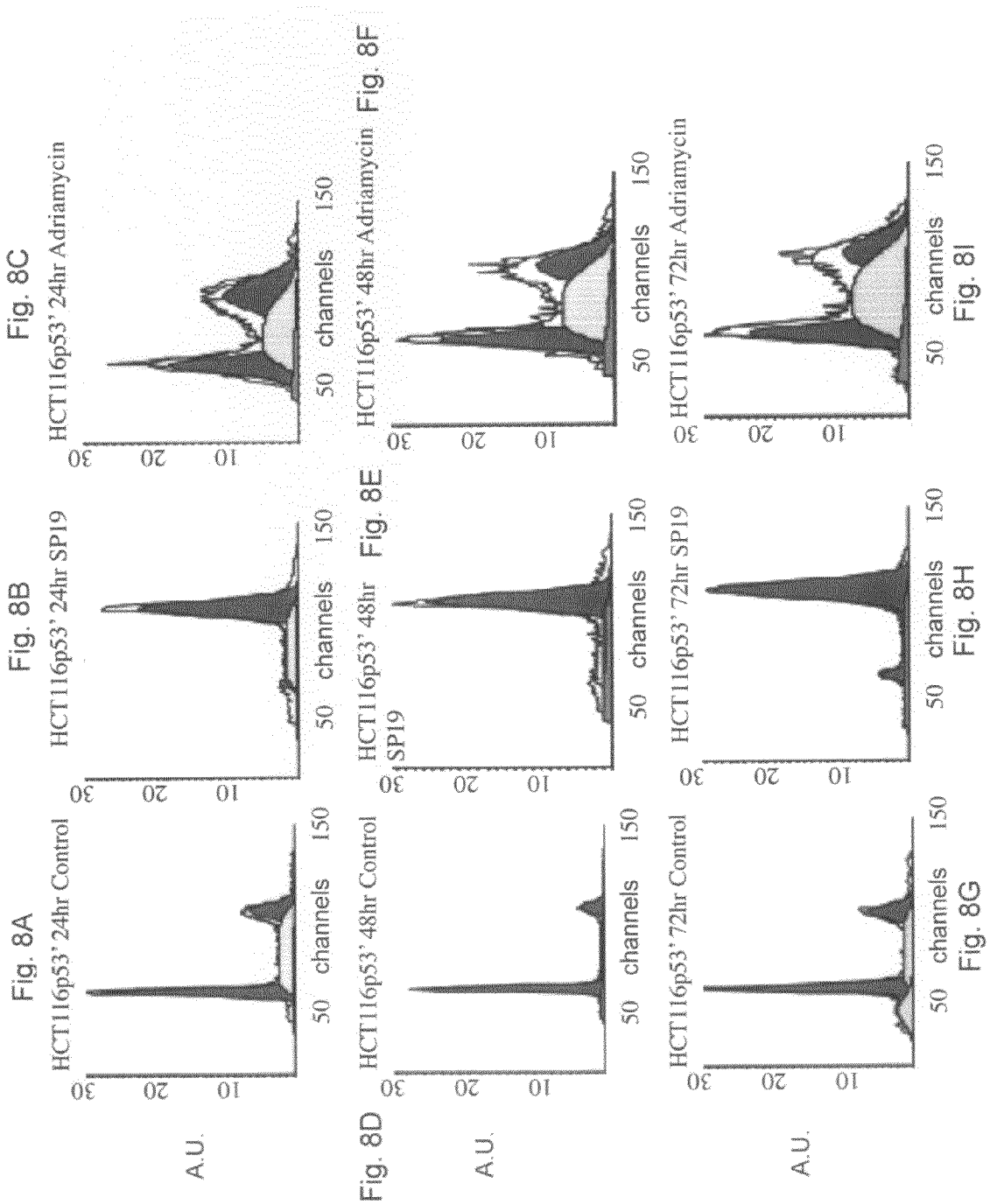

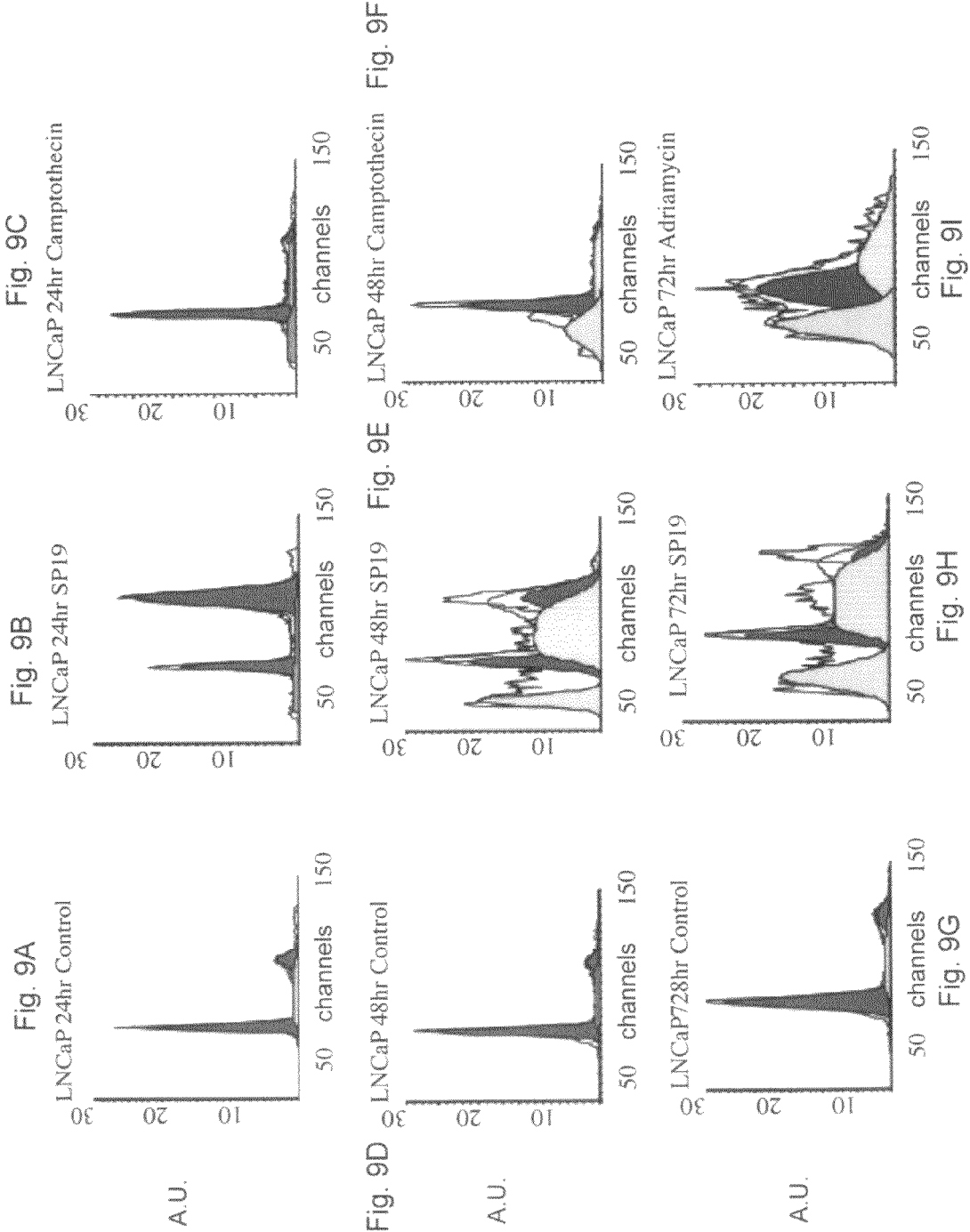

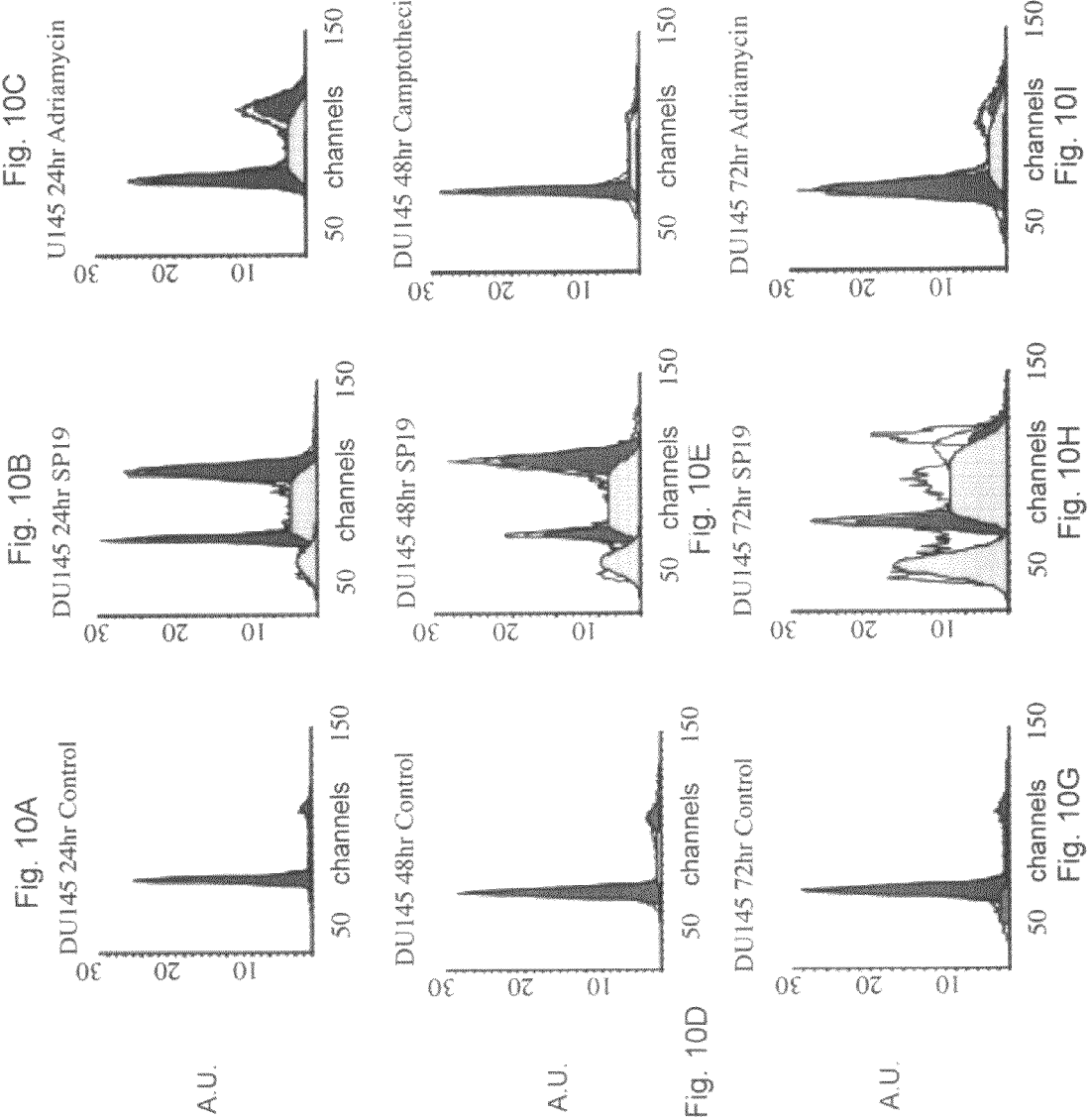

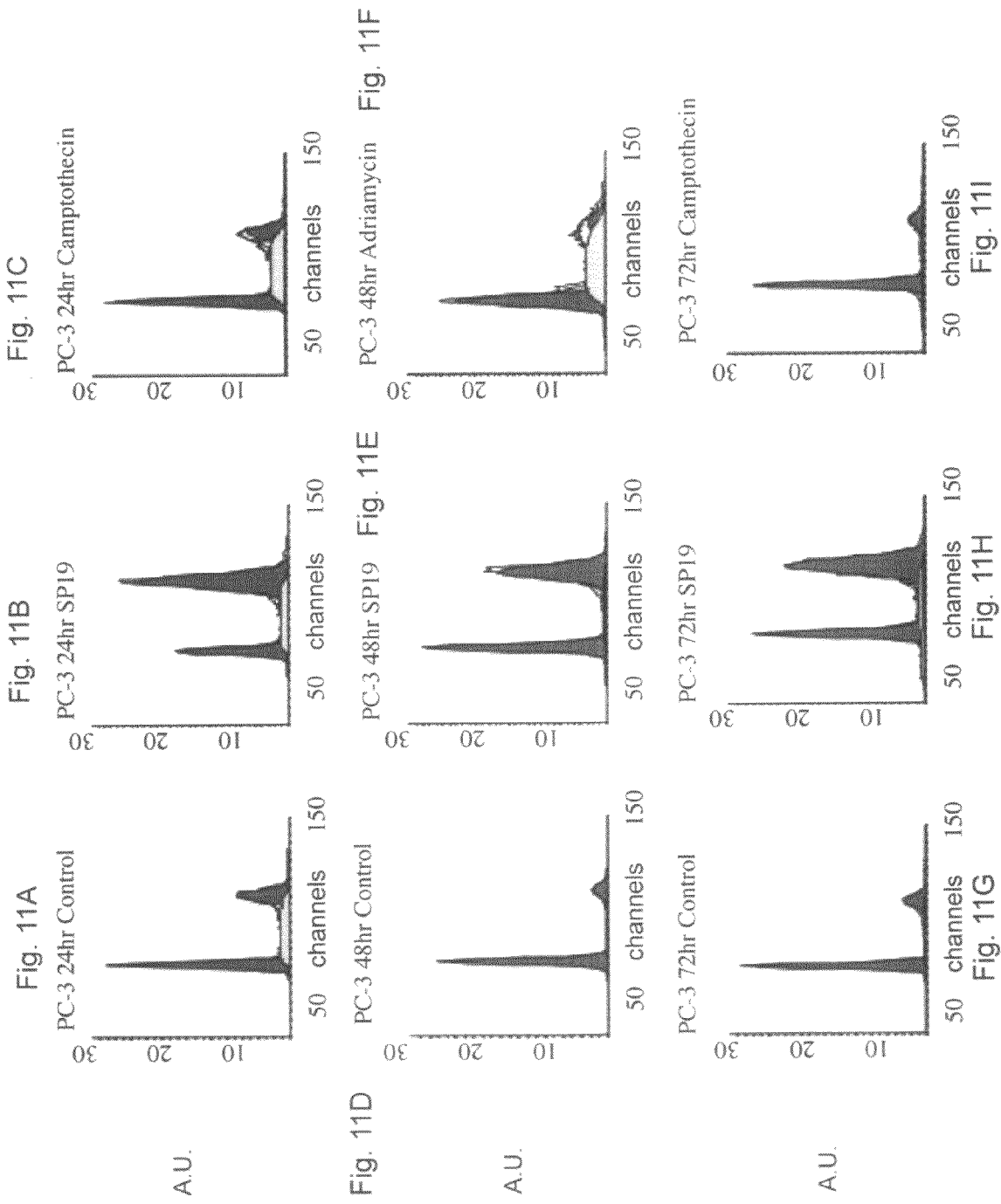

1-ARYL- OR 1-HETEROARYL-PYRIDO[B]INDOLES AND USES THEREOF IN TREATING CANCERS

CROSS-REFERENCE TO RELATED APPLICATIONS

This non-provisional application claims benefit of priority under 35 U.S.C. §119(e) of provisional U.S. Ser. No. 61/214,582, filed Apr. 24, 2009, the entirety of which is hereby incorporated by reference.

FEDERAL FUNDING LEGEND

This invention was made with government support under Grant Number R15CA100102 awarded by National Institutes of Health-National Cancer Institute. The government has certain rights in invention.

BACKGROUND OF THE INVENTION

1. Field of the Invention

The present invention relates to the fields of organic chemistry and chemotherapeutic compounds. Specifically, the present invention relates to 1-aryl (heteroaryl)pyrido[b]indoles and uses thereof in treating cancers.

2. Description of the Related Art

More than half a million people die of cancer every year in the United States, making cancer the second leading cause of death in this country after heart disease. The total economic cost of cancer to the United States has been estimated at over $263 billion. Thus, the need for effective cancer therapies cannot be overstated.

The β-carboline scaffold and reduced derivatives thereof appear to be 'privileged' bioactive structures that occur in a variety of natural products with anticancer activity among other effects (1). For example, the ability of harmine to affect cyclin-dependent kinases and cancer cell proliferation has been described (2). Also, have reported a structure-activity relationship of tetrahydro-β-carbolines as cell cycle arresting agents and inducers of apoptosis has been reported (3). Tangutorine, a β-carboline alkaloid, was recently shown to be an inducer of p21 expression and abnormal mitosis in human colon cancer cells (4). Isostrychnopentam119(eine, an indolomonoterpenic alkaloid containing a tetrahydro-β-carboline moiety induces cell cycle arrest and apoptosis in human colon cancer cells (5).

There is still, however, a recognized need in the art for improved chemotherapeutics and cancer therapies. Specifically, the prior art is deficient in 1-aryl- or 1-heteroarylpyrido[b]indoles, for example substituted β-carbolines effective to inhibit cancer cell proliferation. The present invention fulfills this long standing need in the art.

SUMMARY OF THE INVENTION

The present invention is directed to a β-carboline compound having the structure

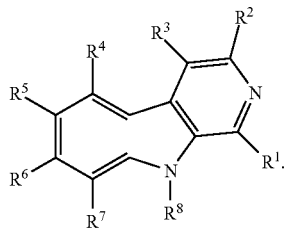

The $R^1$ substituents are phenyl, furanyl, naphthyl, anthracyl, phenanthracyl, quinolinyl, isoquinolinyl, quinoxalinyl, or phenyl substituted with pyridinyl, or $C_1$-$C_4$ alkyl or $C_1$-$C_4$ alkoxy derivatives thereof. The $R^2$-$R^8$ substituents may be independently, hydrogen, $C_1$-$C_4$ alkyl, $C_1$-$C_4$ alkoxy, $C_1$-$C_4$ alkoxyphenyl, halogen, thiol, alkylthiol, sulfonyl, sulfonamide, amide, substituted amide, ester, nitrile, OH, amino, substituted amine, haloalkyl, haloalkoxy, or acyl.

The present invention also is directed to a method for inhibiting cancer cell proliferation. The method comprises contacting cancer cells or a tumor comprising the same with an amount of one or more of the substituted β-carboline compounds described herein effective to inhibit proliferation of the cancer cells.

The present invention is directed further to a method for treating a cell proliferative disease in a subject. The method comprises administering to the subject a pharmacologically effective amount of one or more of the substituted β-carboline compounds described herein to the subject thereby treating the cell proliferative disease. The present invention is directed to a related method further comprising administering one or more other antiproliferative drugs to the patient.

The present invention is directed further still to a synthetic β-carboline compound that is 1-furan-3-yl-6-methoxy-9H-β-carboline, 1-furan-3-yl-7-methoxy-9H-β-carboline, 1-pyridin-3-yl-7-methoxy-9H-β-carboline, 6-methoxy-1-quinolin-4-yl-9H-β-carboline, 7-methoxy-1-quinolin-4-yl-9H-β-carboline, 1-Isoquinolin-1-yl-7-methoxy-9H-β-carboline, 6-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 1-isoquinolin-4-yl-6-methoxy-9H-β-carboline, 1-isoquinolin-4-yl-7-methoxy-9H-β-carboline, 6-methoxy-1-quinolin-3-yl-9H-β-carboline, 7-methoxy-1-quinolin-3-yl-9H-β-carboline, 6-methoxy-1-naphthalen-1-yl-9H-β-carboline, 7-methoxy-1-naphthalen-1-yl-9H-β-carboline, 6-methoxy-1-quinolin-5-yl-9H-β-carboline, 7-methoxy-1-quinolin-5-yl-9H-β-carboline, 6-methoxy-1-quinolin-6-yl-9H-β-carboline, 1-isoquinolin-5-yl-6-methoxy-9H-β-carboline, 1-isoquinolin-5-yl-7-methoxy-9H-β-carboline, 6-methoxy-1-naphthalen-2-yl-9H-β-carboline, 7-methoxy-1-naphthalen-2-yl-9H-β-carboline, 1-anthracen-9-yl-6-methoxy-9H-β-carboline, 1-anthracen-9-yl-7-methoxy-9H-β-carboline, 6-methoxy-1-phenanthren-9-yl-9H-β-carboline, 7-methoxy-1-phenanthren-9-yl-9H-β-carboline, 6-methoxy-1-phenyl-9H-β-carboline, 7-methoxy-1-phenyl-9H-β-carboline, 6-methoxy-1-(2-methyl-naphthalen-1-yl)-9H-β-carboline, 7-methoxy-1-(2-methyl-naphthalen-1-yl)-9H-β-carboline, 6-methoxy-1-(6-methoxy-naphthalen-1-yl)-9H-β-carboline, 6-Benzyloxy-1-naphthalen-1-yl-9H-β-carboline, 8-methyl-1-naphthalen-1-yl-9H-β-carboline, or 6-methoxy-1-(4-pyridin-2-yl-phenyl)-9H-β-carboline. Mono- and multiple-azapyrido[b]indoles also anticipated, as well as g- and d-carbolines and their derivatives.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 4A-4F illustrate flow cytometry histograms comparing the effects of Compound 19 and Camptothecin treatment on the cell cycle kinetics of MCF-7 breast cancer cells.

FIGS. 5A-5F illustrate flow cytometry histograms comparing the effects of Compound 19 and Adriamycin treatment on the cell cycle kinetics of cultured normal human fibroblasts.

FIGS. 6A-6I illustrate flow cytometry histograms showing the effects of Compound 19 and Adriamycin or Camptothecin treatment on the cell cycle kinetics of A549 lung cancer cells.

FIGS. 7A-7I illustrate flow cytometry histograms showing the effects of Compound 19 and Adriamycin treatment on the cell cycle kinetics of HCT116 cells.

FIGS. 8A-8I illustrate flow cytometry histograms showing the effects of Compound 19 and Adriamycin treatment on the cell cycle kinetics of HCT116 cells.

FIGS. 9A-9I illustrate flow cytometry histograms showing the effects of Compound 19 and Adriamycin or Camptothecin treatment on the cell cycle kinetics of LNCaP cells.

FIGS. 10A-10I illustrate flow cytometry histograms showing the effects of Compound 19 and Adriamycin or Camptothecin treatment on the cell cycle kinetics of DU145 cells.

FIGS. 11A-11I illustrate flow cytometry histograms showing the effects of Compound 19 and Adriamycin or Camptothecin treatment on the cell cycle kinetics of PC-3 lung cancer cells.

DETAILED DESCRIPTION OF THE INVENTION

Figure 1A:
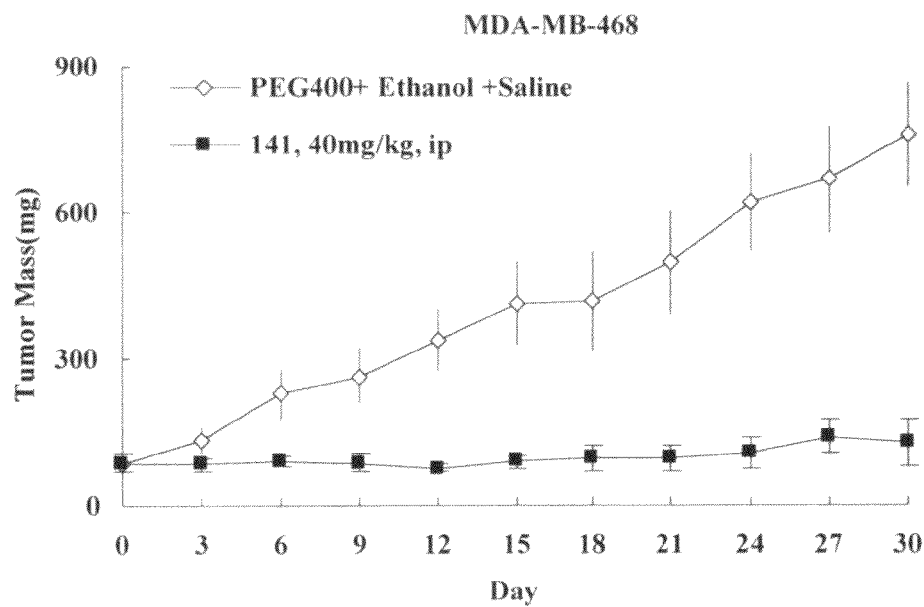
FIGS. 1A-1B illustrate antitumor activity on tumor mass (FIG. 1A) and on body weight (FIG. 1B) of compound 19 treatment in nude mice bearing human MDA-MB-468 breast cancer xenografts.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device, compound, composition, or method described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the terms "compound", "1-aryl(heteroaryl) pyrido[b]indole compound" or "substituted β-carboline compound" may be interchangeable and refer to a chemically synthesized molecular entity or derivatives or analogs thereof, including salts or hydrates, that blocks, stops, inhibits, and/or suppresses cancer cell proliferation and treats the cancer or tumor associated therewith. As would be apparent to one of ordinary skill in the art "aryl" and "heteroaryl" refer to any functional group or substituent derived from a simple aromatic ring(s) or a simple aromatic ring(s) containing a heteroatom, preferably in this instance nitrogen, oxygen or sulfur.

As used herein, the term "contacting" refers to any suitable method of bringing one or more of the compounds described herein with or without one or more other therapeutic agents into contact with one or more cancer cells or a tumor comprising the same. In vitro or ex vivo this is achieved by exposing the cancer cells or tumor to the compound(s)/therapeutic agent(s) in a suitable medium. For in vivo applications, any known method of administration is suitable as described herein.

As used herein, the terms "effective amount", "pharmacologically effective amount" or "therapeutically effective amount" are interchangeable and refer to an amount that results in an antiproliferative effect against cancer cells in vitro or an improvement or remediation in the cancer in vivo. Those of skill in the art understand that the effective amount may improve the patient's or subject's condition, but may not be a complete cure of the cancer.

As used herein, the term "treating" or the phrase "treating a cancer" includes, but is not limited to, halting the growth of the cancer, killing the cancer, or reducing the size of the cancer. Halting the growth refers to halting any increase in the size or the number of or size of the cancer cells or to halting the division of the cancer cells. Reducing the size refers to reducing the size of the tumor associated with the cancer or the number of or size of the cancer cells.

As used herein, the term "subject" refers to any target of the treatment.

In one embodiment of the present invention, there is provided β-carbolines having the structure:

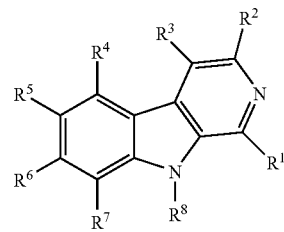

where $R^1$ is phenyl, naphthyl, anthracyl, phenanthracyl, quinolinyl, isoquinolinyl, quinoxalinyl, or phenyl substituted with pyridinyl, or $C_1$-$C_4$ alkyl or $C_1$-$C_4$ alkoxy derivatives thereof; and $R^2$-$R^8$ are independently hydrogen, $C_1$-$C_4$ alkyl, $C_1$-$C_4$ alkoxy, $C_1$-$C_4$ alkoxyphenyl, halogen, thiol, alkylthiol, sulfonyl, sulfonamide, amide, substituted amide, ester, nitrile, OH, amino, substituted amine, haloalkyl, haloalkoxy, or acyl. Particularly, for example, $R^1$ may be 2-, 3-, 4-, 5-, 6-, or 7-benzofuranyl, 2-, 3-, 4-, 5-, 6-, or 7-indolyl, 2-, 3-, 4-, 5-, 6-, or 7-benzothiophenyl, 1-, 2-, 3-, 4-, 5-, or 6-indenyl, 2-, 4-, 5-, 6- or 7-benzoxazolyl, 2-, 4-, 5-, 6- or 7-benzimidazolyl, 2-, 4-, 5-, 6- or 7-benzothiazolyl, 3-furanyl, 3-pyridinyl, 3-, 4- or 5-quinolinyl, 1-, 4- or 5-isoquinolinyl, 5- or 6-quinoxalinyl, 1-naphthyl, 2-methyl- or 6-methoxy-napththalen-1-yl, 9-anthracyl, 9-phenanthracyl, 1-phenyl, 4-pyridin-2-yl-phenyl, or a group having the structure:

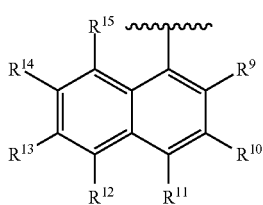

where $R^9$-$R^{15}$ may independently be $C_1$-$C_4$ alkyl, $C_1$-$C_4$ alkoxy, halogen, $C_1$-$C_4$ alkylthiol, sulfonyl, sulfonamide, amide, substituted amide, ester, nitrile, hydroxyl, amino, substituted amine, $C_1$-$C_4$ haloalkyl, $C_1$-$C_4$ haloalkoxy, acyl, aryl, heteroaryl or derivative thereof; and where $R^2$-$R^4$ may be H; $R^5$ may be —$OCH_3$, —$OCH_2$(phenyl) or H; $R^6$ may be —$OCH_3$ or H; $R^7$ may be —$CH_3$ or H; and $R^8$ may be H.

In one aspect of this embodiment $R^1$ may be 3-furanyl, 3-, 4- or 5-quinolinyl, 4- or 5-isoquinolinyl, 5- or 6-quinoxalinyl, 1- or 2-naphthyl, 2-methyl- or 6-methoxy-napthhalen-1-yl, 9-anthracyl, 9-phenanthracyl, 1-phenyl, or 4-pyridin-2-yl-phenyl; $R^5$ may be —$OCH_3$; and $R^6$-$R^7$ may be H.

In another aspect of this embodiment $R^1$ may be 3-furanyl, 3-pyridinyl, 3-, 4- or 5-quinolinyl, 1-, 4- or 5-isoquinolinyl, 5- or 6-quinoxalinyl, 1- or 2-naphthyl, 2-methyl-napththalen-1-yl, 9-anthracyl, 9-phenanthracyl, or 1-phenyl; $R^6$ may be —$OCH_3$; and $R^5$ and $R^7$ may be H.

In yet another aspect of this embodiment $R^1$ may be 1-naphthyl; $R^2$ may be H; $R^6$—$OCH_2$(phenyl); and $R^5$ and $R^7$ may be H.

In yet another aspect of this embodiment $R^1$ may be 1-naphthyl; $R^5$ and $R^6$ may be H; and $R^7$ may be —$CH_3$.

In all aspects of this embodiment the substituted β-carboline compound may be a pharmacologically effective salt or hydrate thereof. Also, the substituted β-carboline may be a pharmaceutical composition further comprising a pharmaceutically effective carrier.

In another embodiment of the present invention, there is provided a method for inhibiting proliferation of cancer cells, comprising contacting cancer cells or a tumor comprising the same with one or more substituted β-carboline compounds described supra thereby inhibiting cancer cell proliferation. In this embodiment the cancer cell may be a breast cancer cell, a colon cancer cell, a prostate cancer cell, a pancreatic cancer cell, or a lung cancer cell.

In one aspect of this embodiment the cancer cell may be contacted in vitro. In another aspect of this embodiment the cancer cell may comprise a tumor contacted in vivo where the method further comprises contacting the tumor with one or more other anticancer drugs. In this other aspect the other anticancer drug(s) may be administered concurrently with or sequentially to the administration of the compound(s).

In yet another embodiment of the present invention, there is provided a method for treating a cell proliferative disease in a subject, comprising administering to the subject a pharmacologically effective amount of one or more substituted β-carboline compounds described supra thereby treating the cell proliferative disease. Further to this embodiment the method comprises administering one or more other anti-proliferative drugs to the subject. In this further embodiment the other anti-proliferative drug(s) may be administered concurrently with or sequentially to the administration of the compound(s).

In both embodiments the cell proliferative disease may be a cancer. Examples of a cancer are a breast cancer, a colon cancer, a prostate cancer, or a pancreatic cancer.

In yet another embodiment of the present invention, there is provided a synthetic β-carboline compound that is 1-furan-3-yl-6-methoxy-9H-β-carboline, 1-furan-3-yl-7-methoxy-9H-β-carboline, 1-pyridin-3-yl-7-methoxy-9H-β-carboline, 6-methoxy-1-quinolin-4-yl-9H-β-carboline, 7-methoxy-1-quinolin-4-yl-9H-β-carboline, 1-Isoquinolin-1-yl-7-methoxy-9H-3-carboline, 6-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 6-methoxy-1-quinoxalin-5-yl-9H-β-carboline, 7-methoxy-1-quinoxalin-5-yl-9H-β-carboline, 1-isoquinolin-4-yl-6-methoxy-9H-β-carboline, 1-isoquinolin-4-yl-7-methoxy-9H-β-carboline, 6-methoxy-1-quinolin-3-yl-9H-β-carboline, 7-methoxy-1-quinolin-3-yl-9H-β-carboline, 6-methoxy-1-naphthalen-1-yl-9H-β-carboline, 7-methoxy-1-naphthalen-1-yl-9H-β-carboline, 6-methoxy-1-quinolin-5-yl-9H-β-carboline, 7-methoxy-1-quinolin-5-yl-9H-β-carboline, 6-methoxy-1-quinolin-5-yl-9H-β-carboline, 1-isoquinolin-5-yl-6-methoxy-9H-β-carboline, 1-isoquinolin-5-yl-7-methoxy-9H-β-carboline, 6-methoxy-1-naphthalen-2-yl-9H-β-carboline, 7-methoxy-1-naphthalen-2-yl-9H-β-carboline, 1-anthracen-9-yl-6-methoxy-9H-β-carboline, 1-anthracen-9-yl-7-methoxy-9H-β-carboline, 6-methoxy-1-phenanthren-9-yl-9H-β-carboline, 7-methoxy-1-phenanthren-9-yl-9H-β-carboline, 6-methoxy-1-phenyl-9H-β-carboline, 7-methoxy-1-phenyl-9H-β-carboline, 6-methoxy-1-(2-methyl-naphthalen-1-yl)-9H-β-carboline, 7-methoxy-1-(2-methyl-naphthalen-1-yl)-9H-β-carboline, 6-methoxy-1-(6-methoxy-naphthalen-1-yl)-9H-β-carboline, 6-Benzyloxy-1-naphthalen-1-yl-9H-β-carboline, 8-methyl-1-naphthalen-1-yl-9H-β-carboline, or 6-methoxy-1-(4-pyridin-2-yl-phenyl)-9H-β-carboline.

Provided herein are chemically synthesized 1-aryl- or 1-heteroarylpyrido[b]indole compounds (1-aryl(heteroaryl) pyrido[b]indole), including derivatives and analogs thereof. These compounds exhibit antiproliferative effects against cell proliferative diseases, such as cancers. Without being limiting, for example, the compounds provided herein are effective against breast cancers, colon cancers, prostate cancers, or pancreatic cancers. Chemical syntheses of these 1-aryl(heteroaryl)pyrido[b]indole compounds are provided in Example 1.

Generally, the 1-aryl(heteroaryl)pyrido[b]indole compounds are small molecule aromatic structures having the chemical structure:

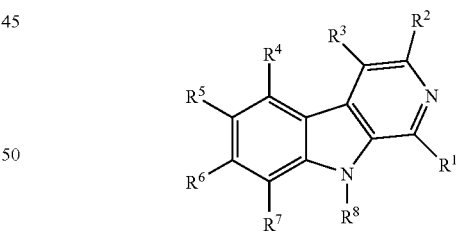

These compounds comprise a β-carboline having an aryl or heteroaryl substituent at C1 on the pyridine moiety. In addition, the indole moiety comprising the β-carboline may be substituted at one or more of C3-C8 and N9 in the pyrido[b] indole ring.

For example, without being limiting, $R^1$ aryl or heteroaryl substitutents at C1 may be phenyl, furanyl, pyridinyl, naphthyl, anthracyl, phenanthracyl, quinolinyl, isoquinolnyl, quinoxalinyl, or phenyl substituted with pyridinyl. It is contemplated that these aryl and heteroaryl substitutents may be substituted with short chain $C_1$-$C_4$ alkyl or alkoxy groups, particularly methyl or methoxy. For example, and without limiting possible substituents, $R^1$ may be a 2-, 3-, 4-, 5-, 6-, or 7-benzofuranyl, 2-, 3-, 4-, 5-, 6-, or 7-indolyl, 2-, 3-, 4-, 5-, 6-, or 7-benzothiophenyl, 1-, 2-, 3-, 4-, 5-, or 6-indenyl, 2-, 4-, 5-, 6- or 7-benzoxazolyl, 2-, 4-, 5-, 6- or 7-benzimidazolyl, 2-, 4-, 5-, 6- or 7-benzothiazolyl 3-furanyl, 3-pyridinyl, 3-, 4- or 5-quinolinyl, 1-, 4- or 5-isoquinolinyl, 5-quinoxalinyl, 1- or 2-naphthalenyl, 2-methyl- or 6-methoxy-naphthalen-1-yl, 9-anthracenyl, 9-phenanthrenyl, phenyl, or 4-pyridin-2-yl-phenyl. Alternatively, $R^1$ may be a group having the structure:

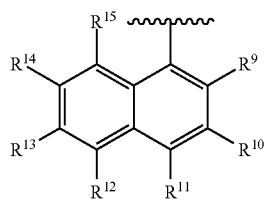

where the $R^9$, $R^{10}$, $R^{11}$, $R^{12}$, $R^{13}$, $R^{14}$, and $R^{15}$ may independently be $C_1$-$C_4$ alkyl, $C_1$-$C_4$ alkoxy, halogen, $C_1$-$C_4$ alkylthiol, sulfonyl, sulfonamide, amide, substituted amide, ester, nitrile, hydroxyl, amino, substituted amine, $C_1$-$C_4$ haloalkyl, $C_1$-$C_4$ haloalkoxy, acyl, aryl, heteroaryl or derivative thereof.

Generally, $R^2$, $R^3$, $R^4$, $R^5$, $R^6$, $R^7$, and $R^8$ substituents at C3-C8 and N9 may be hydrogen or short chain $C_1$-$C_4$ alkyl, alkoxy or aryloxy groups, particularly methyl, methoxy or benzyloxy; halogen, thiol, alkylthiol, sulfonyl, sulfomainde, amide, substituted amide, ester, nitrile, OH, amino, substituted amine, haloalkyl, haloalkoxy, acyl. Examples of 1-aryl (heteroaryl)pyrido[b]indole compounds, particularly β-carbolines derivativeas are provided in Example 2.

Thus, the 1-aryl(heteroaryl)pyrido[b]indole compounds provided herein are useful as therapeutics. The compounds provided herein may be used to treat any subject, preferably a human, having a cell proliferative disease, such as a cancer, for example, but not limited to, a breast cancer, a colon cancer, a prostate cancer or a pancreatic cancer. It is contemplated that contacting the cancer cells comprising a cancer or tumor with one or more of these 1-aryl(heteroaryl)pyrido[b]indole compounds, particularly substituted beta-carbolines is effective to at least inhibit, reduce or prevent cancer cell proliferation or tumor growth. The compounds of the present invention may be administered alone or in combination or in concurrent therapy with other chemotherapeutic agents or pharmaceuticals which affect cancer pathology.

The present invention also provides therapeutic methods employing compositions comprising the 1-aryl(heteroaryl) pyrido[b]indole compounds disclosed herein. Preferably, these compositions include pharmaceutical compositions comprising a therapeutically or pharmacologically effective amount of one or more of the 1-aryl(heteroaryl)pyrido[b] indole compounds along with a pharmaceutically acceptable carrier. Also, these compositions include pharmacologically effective salts or hydrates thereof.

As is well known in the art, a specific dose level of chemotherapeutic compounds, such as the 1-aryl(heteroaryl)pyrido[b]indole compounds or related derivative or analog compounds thereof for any particular patient depends upon a variety of factors including the activity of the specific compound employed, the age, body weight, general health, sex, diet, time of administration, route of administration, rate of excretion, drug combination, and the progression or remission of the cancer. The person responsible for administration is well able to determine the appropriate dose for the individual subject and whether a suitable dosage of either or both of the substituted β-carbinols compound(s) and other chemotherapeutic agent(s) or drug(s) comprises a single administered dose or multiple administered doses.

The following example(s) are given for the purpose of illustrating various embodiments of the invention and are not meant to limit the present invention in any fashion.

EXAMPLE 1

Chemical Synthesis of β-carbolines
Methods and Materials

All the chemicals and solvents were purchased from Aldrich and used without further purification. All the reactions were performed under nitrogen atmosphere. TLC monitored progress of all the reaction on silica gel plates (Analtech, Inc.). Fisher scientific Da visil grade 1740 (170-400 mesh) was used for flash chromatography to purify the final products. $^1$H NMR spectra were recorded on Brucker AR, 300-MHz spectrometer: chemical shifts are expressed in δ values (ppm) reference to the TMS and coupling constants (J values) in Hz. Mass spectral data were determined on a Brucker-HP Esquire-LC spectrometer (ESI-MS). Elemental analysis (C, H, N) was performed by Atlantic Microlab, Inc. (Norcross, G A) and results were within ±0.4% of the theoretical values for the formula given.

General Procedure for the Synthesis of Tetrahydro β-carbolines

5-Methoxy tryptamine 1a or 6-methoxy tryptamine 1b (0.524 mmol) and appropriate aryl or heteroaryl aldehyde 2 (0.63 mmol) were dissolved in THF (20 mL). The reaction mixture was cooled to 0° C. $CF_3COOH$ (0.2 ml) was then added at 0° C., and the reaction mixture was then allowed to stir at 0° C. for 1 hr. The ice bath was then removed and the reaction allowed to stir for a further 1 hr from 0° C. to r.t. The reaction mixture was quenched with aqueous saturated $NaHCO_3$ (5 ml) and the organic phase separated. The mixture was extracted with EtOAc (2×10 ml). The combined organic phase was dried (anhydrous $NaSO_4$), filtered and evaporated in vacuo to give the crude product tetrahydro β-carboline 3. The crude product was directly used for second step with out further purification.

General Procedure for the Synthesis of β-Carbolines

To a solution of the crude tetrahydro β-carboline 3 in xylene (10 ml) was added 10% Pd/C (50-100 mg) and the mixture refluxed overnight. The reaction mixture was then cooled and filtered through celite and washed with MeOH (5-10 ml). Evaporation of the xylene/MeOH filtrate in vacuo yielded a crude β-carboline residue. The crude residue was subjected to flash chromatography to obtain pure β-carbolines 4 (5% MeOH/$CH_2Cl_2$).

General Procedure for the Synthesis of 7-Hydroxy β-carbolines

β-carboline derivative (0.02 mmol) in dry methylene chloride was cooled to −60° C. and boron tribromide (0.06 mmol) of 1M solution in methylene chloride was added drop-wise over a period of 5-10 minutes to the reaction flask at the same temperature. After stirring the reaction mixture for 2 days at room temperature was quenched with methanol (10 mL) at −30° C. and again the mixture was allowed to stir for 4 hours. Methanol was evaporated under reduced pressure and the residue was repeatedly evaporated with methanol and was recrystallized with methanol.

Synthetic β-carboline Derivatives 1-pyridin-3-yl-7-methoxy-9H-β-carboline 5

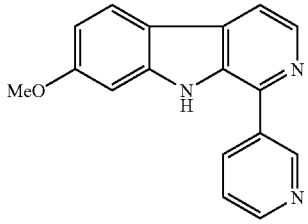

¹H NMR (CD₃)₂CO –d 3.92 (s, 3H), 6.93 (1H, dd, J=2.25 Hz and 8.72 Hz), 7.09 (1H, d, J=2.18 Hz), 7.69 (1H, dd J=4.96 Hz and 7.91 Hz), 8.03 (d, 1H, J=5.34 Hz), 8.08 (d, 1H, J=8.72 Hz), 8.36 (t, 1H), 8.39 (d, 1H, J=5.34 Hz), 8.71 (dd, 1H, J=1.71 Hz and 4.96 Hz), 9.09 (d, 1H, J=1.71 Hz). Anal. calculated for C17H13N3O. 0.1H₂O, (CHN): C, 73.68; H, 4.80; N, 15.16. found C, 73.32; H, 4.76; N, 14.88. MS: m/z 276.2 (MH⁺), m.pt: 216-217° C. MS: m/z 276.3 (MH⁺). (yield 81%).

1-Furan-3-yl-9H-β-carbolin-7-ol 6

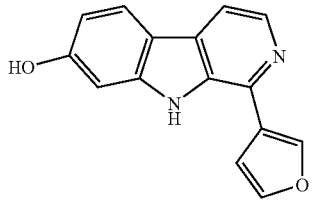

¹H NMR (DMSO-d6): δ 12.12(bs, 1H, OH), 10.55(bs, 1H, NH), 8.82(s, 1H, ArH), 8.62-8.30(m, 3H, ArH), 8.14(d, J=7.8 Hz, 1H, ArH), 7.36 (s, 1H, ArH), 7.24-7.03(m, 1H, ArH), 6.93 (d, J=8.1 Hz, 1H, ArH); MS (ESI); m/z 251 [M+H]⁺; Anal. Calcd. (C₁₅H₁₀N₂O₂) C, H, N.

1-Isopropyl-9H-β-carbolin-7-ol 7

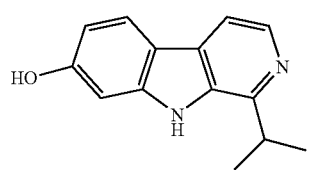

¹H NMR (DMSO-d6): δ 12.48 (bs, 1H, OH), 10.50 (bs, 1H, NH), 8.46-8.25(m, 3H, ArH), 7.05 (s, 1H, ArH), 6.90(d, J=9 Hz, 1H, ArH), 3.95-3.81(m, 1H, CH), 1.52(s, 3H, CH₃) & 1.50(s, 3H, CH₃); MS (ESI); m/z 227 [M+H]⁺; Anal. Calcd. (C₁₄H₁₄N₂O) C, H, N.

1-Furan-3-yl-7-methoxy-9H-β-carboline 8

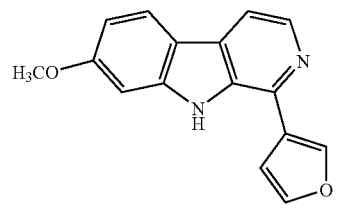

¹H NMR [300 MHz, (CD₃)₂CO]: d 3.92 (s, 3H), 6.92 (1H, dd, J=2.25 Hz and 8.67 Hz), 7.16 (1H, d, J=2.25 Hz), 7.27 (dd, 1H, J=0.79 Hz and 1.82 Hz), 7.77 (t, 1H), 7.91 (d, 1H, J=5.18 Hz), 8.11 (d, 1H, J=8.67 Hz), 8.39 (d, J=5.18 Hz, 1H), 8.46 (d, J=0.79 Hz, 1H), 10.37 (bs, 1H). MS: m/z 265.1 (MH⁺), 401.5 (m+Na). m.pt: 203-204° C. (yield 56%).

1-Furan-3-yl-6-methoxy-9H-β-carboline 9

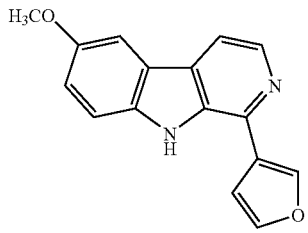

¹H NMR (CDCl₃): δ 8.53 (bs, 1H, NH), 8.48(d, J=5.1 Hz, 1H, ArH), 8.14 (s, 1H, ArH), 7.85(d, J=75.4 Hz, 1H, ArH), 7.61 (s, 1H, ArH), 7.57(s, 1H, ArH), 7.42 (d, J=9.0 Hz, 1H, ArH), 7.21 (dd, J=2.4, 2.4 Hz, 1H, ArH), 7.11 (s, 1H, ArH), 3.95 (s, 3H, OCH₃), MS (ESI); m/z 265.0 [M+H]⁺; Anal. Calcd. (C₁₆H₁₂N₂O₂) C, H, N. Molecular weight: 264.09

7-Methoxy-1-quinolin-4-yl-9H-β-carboline 10

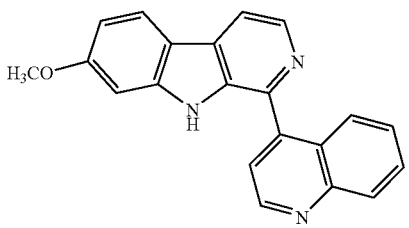

¹H NMR [300 MHz, (CD₃)₂CO]: δ 3.88 (s, 3H), 6.94 (dd, J=2.25 Hz and 8.68 Hz, 1H), 7.00 (d, J=2.25 Hz, 1H), 7.52-7.57 (m, 1H), 7.77 (d, J=4.36 Hz, 1H), 7.79-7.83 (m, 1H), 7.93 (d, J=8.45 Hz, 1H), 8.14 (d, J=5.22 Hz, 1H), 8.18 (d, J=8.34 Hz, 1H), 8.19 (d, J=8.68 Hz, 1H), 8.56 (d, J=5.23 Hz, 1H), 9.01 (d, J=4.36 Hz, 1H), 10.39 (bs, 1H). Anal. Calculated for (C21H15N3O), (CHN) C, 77.52; H, 4.65; N, 12.91. found C, 77.43; H, 4.61; N, 12.85. MS: m/z 326.2 (MH⁺). m.pt: 238-239° C. (yield 79%). Molecular weight: 325.12.

6-Methoxy-1-quinolin-4-yl-9H-β-carboline 11

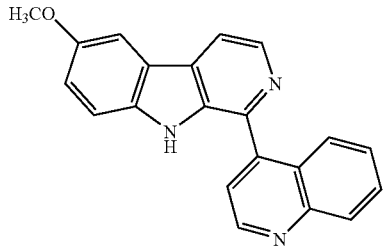

¹H NMR (CDCl₃): δ 9.66(bs, 1H, NH), 8.76(d, J=4.5 Hz, 1H, ArH), 8.65 (d, J=5.4 Hz, 1H, ArH), 8.10(d, J=5.4 Hz, 1H, ArH), 8.04(d, J=8.7 Hz, 1H, ArH), 7.80(d, J=8.7 Hz, 1H, ArH), 7.70-7.59(m, 3H, ArH), 7.51-7.44(m, 3H, ArH), and 4.00(s, 3H, OCH₃); MS (ESI); m/z 348.1 [M+Na]⁺; Anal. Calcd. (C₂₁H₁₅N₃O) C, H, N. Molecular weight: 325.12.

1-Isoquinolin-1-yl-7-methoxy-9H-β-carboline 12

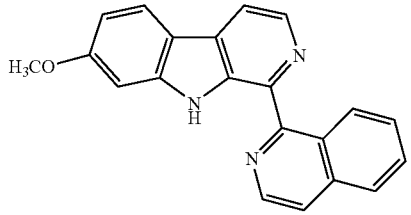

¹H NMR [300 MHz, (CD₃)₂CO]: δ 3.97 (s, 3H), 6.95 (dd, J=2.30 Hz and 8.67 Hz, 1H), 7.43 (d, J=2.25 Hz, 1H), 7.64-7.69 (m, 1H), 7.83-7.89 (m, 1H), 8.05 (d, J=8.03 Hz, 1H), 8.17 (d, J=8.67 Hz, 1H), 8.48-8.56 (m, 4H), 8.96 (d, J=8.71 Hz, 1H), 12.02 (bs, 1H). MS: m/z 326.3 (MH⁺), 348.2 (m+Na). Anal. Calculated for (C21H15N3O), (CHN) C, 77.52; H, 4.65; N, 12.91. found C, 77.74; H, 4.68; N, 13.01. MS: m/z 326.2 (MH+), 348.2 (m+Na). m.pt: 196-197° C. (yield 82%). Molecular weight: 325.12.

6-Methoxy-1-quinoxalin-5-yl-9H-β-carboline Cmpd 13

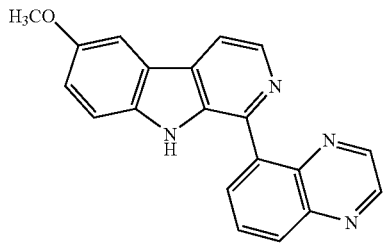

¹H NMR (CDCl₃): δ 8.93(s, 2H, ArH), 8.73(d, J=1.8 Hz, 2H, ArH), 8.65 (d, J=5.1 Hz, 1H, ArH), 8.56(dd, J=1.8 and 1.8 Hz, 1H, ArH), 8.00(d, J=85.4 Hz, 1H, ArH), 7.64 (d, J=2.4

Hz, 1H, ArH), 7.48(d, J=9.0 Hz, 1H, ArH), 7.27(s, 1H, ArH), and 3.98(s, 3H, OCH₃); MS (ESI); m/z 325.1 [M–H]⁻; Anal. Calcd. (C₂₀H₁₄N₄O) C, H, N.

7-Methoxy-1-quinoxalin-5-yl-9H-β-carboline Cmpd 14

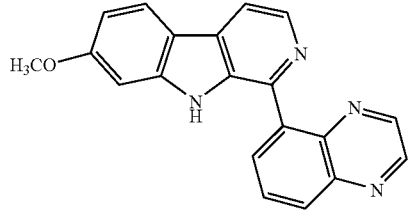

¹H NMR (CDCl₃): δ 11.45(bs, 1H, NH), 8.90(d, J=8.7 Hz, 1H, ArH), 8.71 (s, 1H, ArH), 8.54-8.42(m, 2H, ArH), 8.22(d, J=8.7 Hz, 1H, ArH), 8.02-7.86(m, 2H, ArH), 7.10(s, 1H, ArH), 6.84(dd, J=2.4 and 2.4 Hz, 1H, ArH), and 3.81(s, 3H, OCH₃); MS (ESI); m/z 325.1 [M–H]⁻; Anal. Calcd. (C₂₀H₁₄N₄O) C, H, N.

6-Methoxy-1-quinoxalin-6-yl-9H-β-carboline 13a

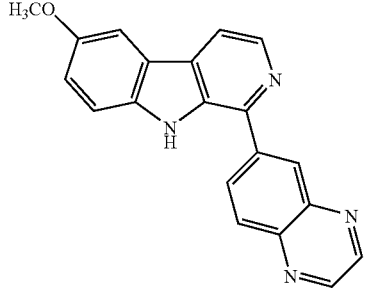

¹H NMR (CDCl₃): δ 11.45(bs, 1H, NH), 8.90(d, J=8.7 Hz, 1H, ArH), 8.71 (s, 1H, ArH), 8.54-8.42(m, 2H, ArH), 8.22(d, J=8.7 Hz, 1H, ArH), 8.02-7.86(m, 2H, ArH), 7.10(s, 1H, ArH), 6.84(dd, J=2.4 and 2.4 Hz, 1H, ArH), and 3.81(s, 3H, OCH₃); MS (ESI); m/z 325.1 [M–H]⁻; Anal. Calcd. (C₂₀H₁₄N₄O) C, H, N. Molecular weight: 326.35.

7-Methoxy-1-quinoxalin-6-yl-9H-β-carboline 14a

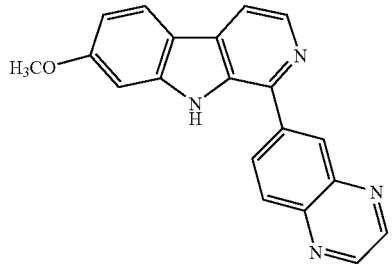

¹H NMR (CDCl₃): δ 8.93(s, 2H, ArH), 8.73(d, J=1.8 Hz, 2H, ArH), 8.65 (d, J=5.1 Hz, 1H, ArH), 8.56(dd, J=1.8 and 1.8 Hz, 1H, ArH), 8.00(d, J=85.4 Hz, 1H, ArH), 7.64 (d, J=2.4 Hz, 1H, ArH), 7.48(d, J=9.0 Hz, 1H, ArH), 7.27(s, 1H, ArH), and 3.98(s, 3H, OCH₃); MS (ESI); m/z 325.1 [M−H]⁻; Anal. Calcd. (C₂₀H₁₄N₄O) C, H, N. Molecular weight: 326.35.

1-Isoquinolin-4-yl-6-methoxy-9H-β-carboline 15

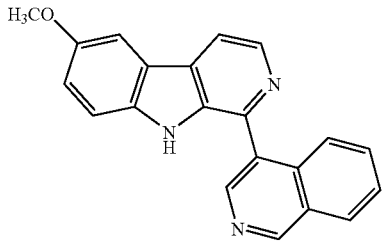

¹H NMR (CDCl₃): δ 10.62(bs, 1H, NH), 8.82(s, 1H, ArH), 8.76(s, 1H, ArH), 8.61(d, J=4.5 Hz, 1H, ArH), 8.04(d, J=5.4 Hz, 1H, ArH), 7.96(d, J=7.5 Hz, 1H, ArH), 7.81-7.60(m, 4H, ArH), 7.42-7.17(m, 2H, ArH), and 3.96(s, 3H, OCH₃); MS (ESI); m/z 324.0 [M−H]⁻; Anal. Calcd. (C₂₁H₁₅N₃O) C, H, N. Molecular weight: 325.12.

1-Isoquinolin-4-yl-7-methoxy-9H-β-carboline 16

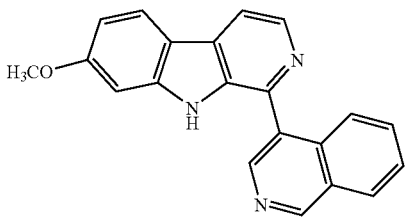

¹H NMR (CDCl₃): δ 11.67(bs, 1H, NH), 8.78(s, 1H, ArH), 8.56(d, J=5.1 Hz, 1H, ArH), 8.49(s, 1H, ArH), 8.12-7.92(m, 2H, ArH), 7.79-7.58(m, 3H, ArH), 7.87-7.96(m, 2H, ArH), and 3.81(s, 3H, OCH₃); MS (ESI); m/z 324.1 [M−H]⁻; Anal. Calcd. (C₂₁H₁₅N₃O) C, H, N. Molecular weight: 325.12.

6-Methoxy-1-Quinolin-3-yl-9H-β-carboline 17

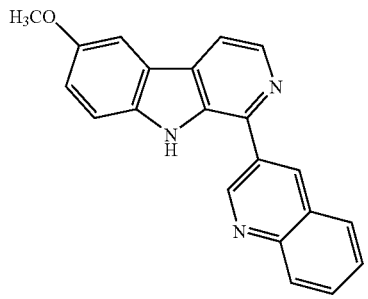

¹H NMR (DMSO-d6): δ 11.67(bs, 1H, NH), 9.53(s, 1H, ArH), 8.97(s, 1H, ArH), 8.52(d, J=5.1 Hz, 1H, ArH), 8.27-8.10(m, 3H, ArH), 7.92-7.80(m, 2H, ArH), 7.29(t, J=6.9 Hz, 1H, ArH), 7.58 (d, J=9.0 Hz, 1H, ArH), 7.24 (d, J=9.0 Hz, 1H, ArH), and 3.89(s, 3H, OCH₃); MS (ESI); m/z 324.0 [M−H]; Anal. Calcd. (C₂₁H₁₅N₃O) C, H, N. Molecular weight: 325.12.

7-Methoxy-1-quinolin-3-yl-9H-β-carboline 18

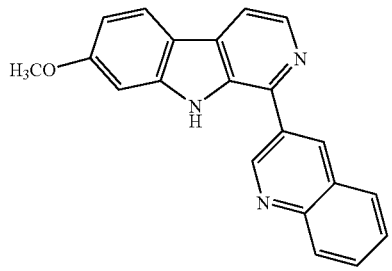

¹H NMR (DMSO-d6): δ 9.58(s, 1H, ArH), 8.82(s, 1H, ArH), 8.52(d, J=5.1 Hz, 1H, ArH), 8.16(d, J=8.4 Hz, 1H, ArH), 8.00(d, J=8.7 Hz, 1H, ArH), 7.90(d, J=5.1 Hz, 1H, ArH), 7.29(t, J=7.2 Hz, 1H, ArH), 7.63(t, J=7.2 Hz, 1H, ArH), 7.55 (s, 1H, ArH), 7.07(s, 1H, ArH), 6.90(d, J=8.4 Hz, 1H, ArH), and 3.91(s, 3H, OCH₃); MS (ESI); m/z 324.0 [M−H]; Anal. Calcd. (C₂₁H₁₅N₃O) C, H, N. Molecular weight: 325.12.

6-Methoxy-1-naphthalen-1-yl-9H-β-carboline 19

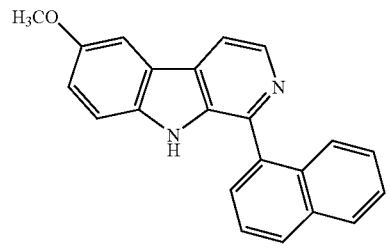

¹H NMR (CDCl₃): δ 8.56(d, J=11.4 Hz, 1H, ArH), 8.21(bs, 1H, NH), 8.04-7.87(m, 3H, ArH), 7.81-7.69(m, 2H, ArH), 7.65-7.37(m, 4H, ArH), 7.23-7.10(m, 2H, ArH), and 3.95(s, 3H, OCH₃); MS (ESI); m/z 323.0 [M−H]⁻; Anal. Calcd. (C₂₂H₁₆N₂O) C, H, N. Molecular weight: 324.13.

7-Methoxy-1-naphthalen-1-yl-9H-β-carboline 20

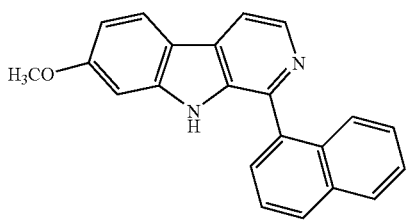

¹H NMR (CDCl₃): δ 8.58(d, J=5.4 Hz, 1H, ArH), 8.09(bs, 1H, NH), 8.07-7.90(m, 4H, ArH), 7.76(t, J=8.4 Hz, 2H, ArH), 7.65-7.40(m, 3H, ArH), 6.92(d, J=8.7 Hz, 1H, ArH), 6.76(s,

1H, ArH), and 3.83(s, 3H, OCH₃); MS (ESI); m/z 323.0 [M–H]⁻; Anal. Calcd. (C₂₂H₁₆N₂O) C, H, N. Molecular weight: 324.13.

6-Methoxy-1-quinolin-5-yl-9H-β-carboline 21

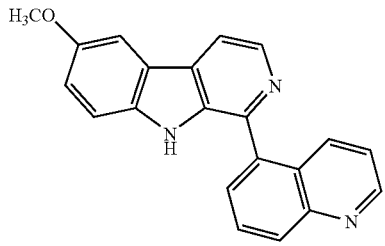

¹H NMR (DMSO-d6): δ 11.00(bs, 1H, NH), 8.94(s, 1H, ArH), 8.48(d, J=5.1 Hz, 1H, ArH), 8.19 (d, J=8.7 Hz, 2H, ArH), 8.05-7.85(m, 3H, ArH), 7.53-7.38(m, 2H, ArH), 7.16 (d, J=8.7 Hz, 1H, ArH), and 3.88(s, 3H, OCH₃); MS (ESI); m/z 324.0 [M–H]; Anal. Calcd. (C₂₁H₁₅N₃O) C, H, N. Molecular weight: 325.12.

7-Methoxy-1-quinolin-5-yl-9H-β-carboline 22

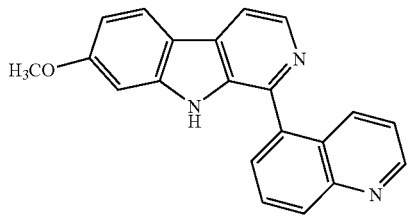

¹H NMR (DMSO-d6): δ 8.97(s, 1H, ArH), 8.60(d, J=5.4 Hz, 1H, ArH), 8.30-8.20(m, 2H, ArH), 8.06(d, J=8.7 Hz, 2H, ArH), 8.00-7.90(m, 2H, ArH), 7.32(dd, J=4.2 and 4.2 Hz, 1H, ArH), 6.96(s, 1H, ArH), 6.89(dd, J=2.1 and 2.1 Hz, 1H, ArH), and 3.90(s, 3H, OCH₃); MS (ESI); m/z 324.0 [M–H]; Anal. Calcd. (C₂₁H₁₅N₃O) C, H, N. Molecular weight: 325.12.

1-Isoquinolin-5-yl-6-methoxy-9H-β-carboline 23

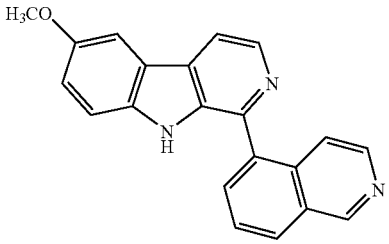

¹H NMR (CDCl₃): δ 9.65(bs, 1H, NH), 8.85(s, 1H, ArH), 8.56(d, J=5.4 Hz, 1H, ArH), 8.24 (d, J=6.0 Hz, 1H, ArH), 8.05-7.85(m, 3H, ArH), 7.75-7.63(m, 3H, ArH), 7.49 (d, J=6.0 Hz, 1H, ArH), 7.35(d, J=9.0 Hz, 1H, ArH), 7.18(dd, J=2.4 and 2.4 Hz, 1H, ArH), and 3.96(s, 3H, OCH₃); MS (ESI); m/z 323.9 [M–H]; Anal. Calcd. (C₂₁H₁₅N₃O) C, H, N. Molecular weight: 325.12.

1-Isoquinolin-5-yl-7-methoxy-9H-β-carboline 24

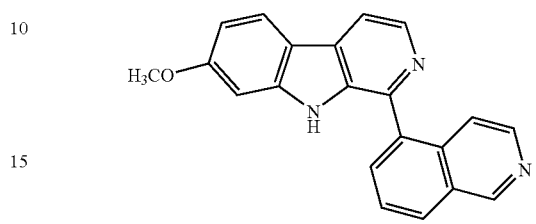

¹H NMR (CDCl₃): δ 9.20(s, 1H, ArH), 8.62(d, J=5.4 Hz, 1H, ArH), 8.53(bs, 1H, NH), 8.42 (d, J=6.0 Hz, 1H, ArH), 8.20-8.03(m, 3H, ArH), 7.80(t, J=8.1 Hz, 1H, ArH), 7.62(d, J=6.0 Hz, 1H, ArH), 6.96(dd, J=2.4 and 2.4 Hz, 1H, ArH), 6.89(s, 1H, ArH), and 3.88(s, 3H, OCH₃); MS (ESI); m/z 323.9 [M–H]; Anal. Calcd. (C₂₁H₁₅N₃O) C, H, N. Molecular weight: 325.12.

6-Methoxy-1-naphthalen-2-yl-9H-β-carboline 25

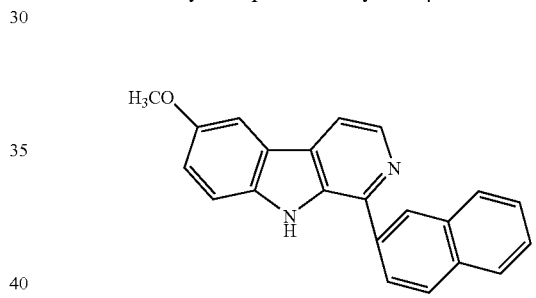

¹H NMR (CDCl₃ and DMSO-d6): δ 8.58-8.43(m, 2H, ArH), 8.14(d, J=8.4 Hz, 1H, ArH), 8.06-7.885(m, 4H, ArH), 7.64-7.46(m, 4H, ArH), 8.16(d, J=8.1 Hz, 1H, ArH), and 3.92(s, 3H, OCH₃); MS (ESI); m/z 323.1 [M–H]⁻; Anal. Calcd. (C₂₂H₁₆N₂O) C, H, N. Molecular weight: 324.13.

7-Methoxy-1-naphthalen-2-yl-9H-β-carboline 26

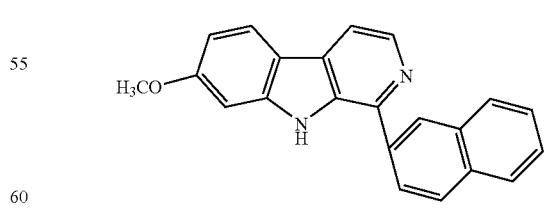

¹H NMR (CDCl₃): δ 8.78(bs, 1H, NH), 8.56(d, J=5.4 Hz, 1H, ArH), 8.35(s, 1H, ArH), 8.12-7.97(m, 3H, ArH), 7.96-7.83(m, 3H, ArH), 7.60-7.48(m, 2H, ArH), 6.96(s, 1H, ArH), and 3.90(s, 3H, OCH₃); MS (ESI); m/z 323.2 [M–H]⁻; Anal. Calcd. (C₂₂H₁₆N₂O) C, H, N. Molecular weight: 324.13.

1-Anthracen-9-yl-6-methoxy-9H-β-carboline 27

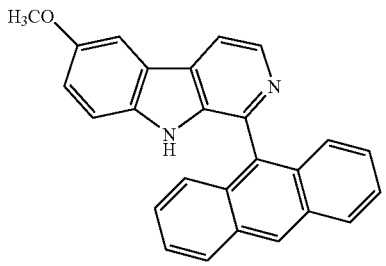

¹H NMR (CDCl₃): δ 8.72(d, J=5.1 Hz, 1H, ArH), 8.64(s, 1H, NH), 8.20-8.08(m, 3H, ArH), 7.68(s, 1H, ArH), 7.62(s, 1H, ArH), 7.53-7.45(m, 3H, ArH), 7.39-7.27(m, 2H, ArH), 7.13(s, 2H, ArH), and 3.97(s, 3H, OCH₃); MS (ESI); m/z 373.0 [M−H]⁻; Anal. Calcd. (C₂₆H₁₈N₂O) C, H, N. Molecular weight: 374.14.

1-Anthracen-9-yl-7-methoxy-9H-β-carboline 28

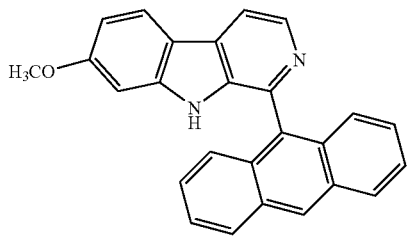

¹H NMR (CDCl₃): δ 9.49(s, 1H, NH), 8.70-8.59(m, 2H, ArH), 8.15-8.00 (m, 4H, ArH), 7.55-7.40(m, 4H, ArH), 7.30 (d, J=7.8 Hz, 2H, ArH), 6.77(dd, J=2.1 and 2.1 Hz, 1H, ArH), 6.78(s, 3H, ArH), and 3.79(s, 3H, OCH₃); MS (ESI); m/z 373.1 [M−H]⁻; Anal. Calcd. (C₂₆H₁₈N₂O) C, H, N. Molecular weight: 374.14.

6-Methoxy-1-phenanthren-9-yl-9H-β-carboline 29

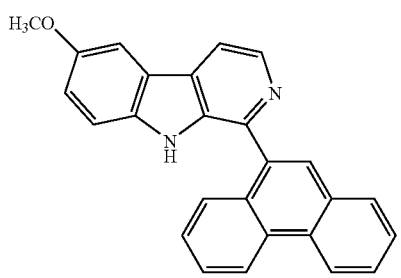

¹H NMR (CDCl₃): δ 8.79(t, J=8.7 Hz, 2H, ArH), 8.55(d, J=5.1 Hz, 1H, ArH), 8.05-7.94(m, 3H, ArH), 7.81(d, J=8.1 Hz, 1H, ArH), 7.76-7.61 (m, 4H, ArH), 7.49(t, J=7.8 Hz, 2H, ArH), 7.36(d, J=8.7 Hz, 1H, ArH), 7.13(dd, J=2.4 and 2.4 Hz, 1H, ArH), and 3.93(s, 3H, OCH₃); MS (ESI); m/z 373.0 [M−H]⁻; Anal. Calcd. (C₂₆H₁₈N₂O) C, H, N. Molecular weight: 374.14.

7-Methoxy-1-phenanthren-9-yl-9H-β-carboline 30

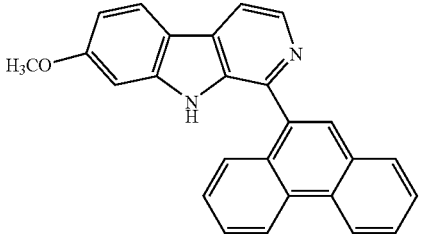

¹H NMR (CDCl₃): δ 8.80(d, J=8.1 Hz, 1H, ArH), 8.75(d, J=8.1 Hz, H, ArH), 8.58(d, J=5.4 Hz, 1H, ArH), 8.17(s, 1H, NH), 8.08-7.88(m, 4H, ArH), 7.82-7.60 (m, 4H, ArH), 7.50(t, J=7.8 Hz, 2H, ArH), 6.92(dd, J=2.1 and 2.1 Hz, 1H, ArH), 6.73(s, 1H, ArH), and 3.80(s, 3H, OCH₃); MS (ESI); m/z 373.0 [M−H]⁻; Anal. Calcd. (C₂₆H₁₈N₂O) C, H, N. Molecular weight: 374.14.

6-Methoxy-1-phenyl-9H-β-carboline 31

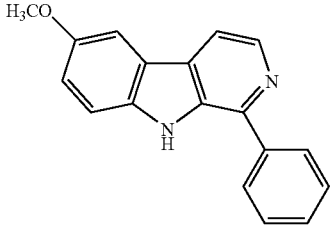

¹H NMR (CDCl₃): δ 8.81(bs, 1H, NH), 8.52(d, J=5.4 Hz, 1H, ArH), 7.97-7.86 (m, 3H, ArH), 7.58(s, 1H, ArH), 7.55-7.32 (m, 4H, ArH), 7.19 (d, J=9.0 Hz, 1H, ArH), and 3.94(s, 3H, OCH₃); MS (ESI); m/z 273.0 [M−H]⁻; Anal. Calcd. (C₁₈H₁₄N₂O) C, H, N. Molecular weight: 274.11.

7-Methoxy-1-phenyl-9H-β-carboline 32

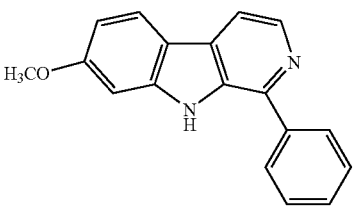

¹H NMR (CDCl₃): δ 8.54(d, J=5.4 Hz, 2H, ArH), 8.06-7.93 (m, 3H, ArH), 7.84(d, J=5.1 Hz, 1H, ArH), 7.58(t, J=7.8 Hz, 2H, ArH), 7.48(t, J=7.6 Hz, 1H, ArH), 6.97-6.92 (m, 2H, ArH), and 3.91(s, 3H, OCH₃); MS (ESI); m/z 273.0 [M−H]⁻; Anal. Calcd. (C₁₈H₁₄N₂O) C, H, N. Molecular weight: 274.11.

6-Methoxy-1-(2-methyl-naphthalen-1-yl)-9H-β-carboline 33

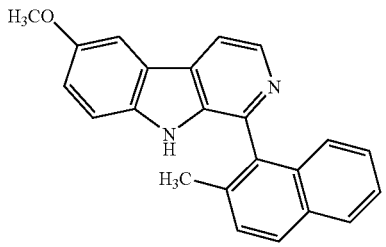

¹H NMR (CDCl₃): δ 8.59(d, J=5.4 Hz, 1H, ArH), 7.80(d, J=5.4 Hz, 1H, ArH), 8.91(d, J=8.4 Hz, 2H, ArH), 7.82(bs, 1H, NH), 7.65(s, 1H, ArH), 7.54-7.40(m, 2H, ArH), 7.34-7.12(m, 4H, ArH), and 3.96 (s, 3H, OCH₃); MS (ESI); m/z 339.2 [M+H]⁺⁻; Anal. Calcd. (C₂₃H₁₈N₂O) C, H, N. Molecular weight: 338.14.

7-Methoxy-1-(2-methyl-naphthalen-1-yl)-9H-β-carboline 34

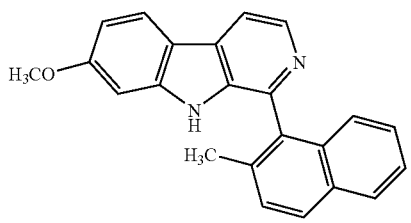

¹H NMR (CDCl₃): δ 8.53(d, J=5.4 Hz, 1H, ArH), 7.05(d, J=5.4 Hz, 1H, ArH), 8.01(bs, 1H, NH), 7.94-7.85(m, 3H, ArH), 7.51-7.37(m, 2H, ArH), 7.31-7.21(m, 2H, ArH), 6.90 (dd, J=2.4 and 2.4 Hz, 1H, ArH), 6.65(s, 1H, ArH), and 3.75(s, 3H, OCH₃); MS (ESI); m/z 339.2 [M+H]⁺⁻; Anal. Calcd. (C₂₃H₁₈N₂O) C, H, N. Molecular weight: 338.14.

6-Methoxy-1-(6-methoxy-naphthalen-1-yl)-9H-β-carboline 35

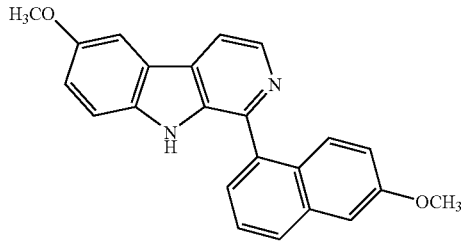

¹H NMR (CDCl₃): δ 8.69(bs, 1H, NH), 8.57(d, J=5.4 Hz, 1H, ArH), 8.31 (s, 1H, ArH), 8.05(dd, J=1.5 and 1.5 Hz, 1H, ArH), 7.92-7.79(m, 3H, ArH), 7.61(s, 1H, ArH), 7.43(d, J=9.0 Hz, 1H, ArH), 7.30-7.15(m, 3H, ArH), 3.97(s, 3H, OCH₃), and 3.96(s, 3H, OCH₃); MS (ESI); m/z 353.0 [M−H]⁻; Anal. Calcd. (C₂₃H₁₈N₂O₂) C, H, N. Molecular weight: 354.14.

6-Benzyloxy-1-naphthalen-1-yl-9H-β-carboline 36

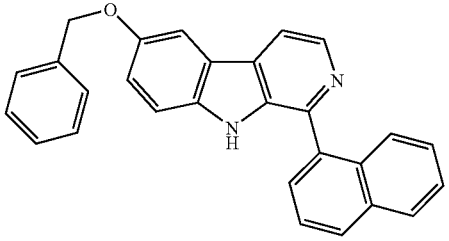

¹H NMR (CDCl₃): δ 8.59(d, J=5.4 Hz, 1H, ArH), 8.10-7.96 (m, 4H, ArH), 7.81-7.71(m, 3H, ArH), 7.65-7.54(m, 4H, ArH), 7.48-7.35(m, 4H, ArH), 7.23(s, 1H, ArH), and 5.22(s, 2H, OCH₂); MS (ESI); m/z 401.0 [M+H]⁺⁻; Anal. Calcd. (C₂₈H₂₀N₂O) C, H, N. Molecular weight: 400.

8-Methyl-1-naphthalen-1-yl-9H-β-carboline 37

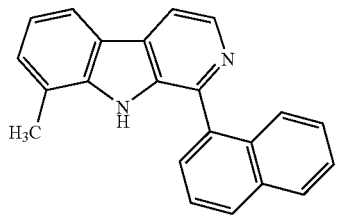

¹H NMR (CDCl₃): δ 8.67(d, J=5.1 Hz, 1H, ArH), 8.12-7.98 (m, 3H, ArH), 7.86-7.67(m, 3H, ArH), 7.57(t, J=6.9 Hz, 1H, ArH), 7.45(t, J=6.9 Hz, 1H, ArH), 7.36 (d, J=7.2 Hz, 1H, ArH), 7.30-7.25(m, 2H, ArH), and 2.43(s, 3H, CH₃); MS (ESI); m/z 307.1 [M−H]⁻; Anal. Calcd. (C₂₂H₁₆N₂) C, H, N. Molecular weight: 308.13.

6-Methoxy-1-(4-pyridin-2-yl-phenyl)-9H-β-carboline 38

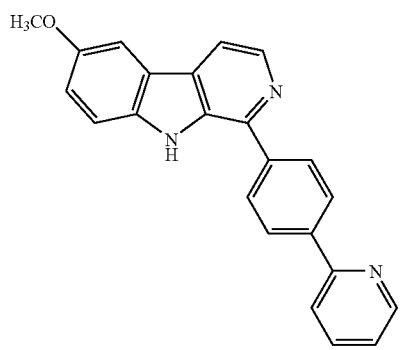

¹H NMR (CDCl₃): δ 9.21(bs, 1H, NH), 8.70(s, 1H, ArH), 8.52(d, J=5.1 Hz, 1H, ArH), 8.10-7.86 (m, 5H, ArH), 7.78-7.54 (m, 3H, ArH), 7.40(d, J=8.7 Hz, 1H, ArH), 7.30-7.15 (m,

2H, ArH), and 3.94(s, 3H, OCH$_3$); MS (ESI); m/z 352.3 [M+H]; Anal. Calcd. (C$_{23}$H$_{17}$N$_3$O) C, H, N. Molecular weight: 351.14.

EXAMPLE 2

Antiproliferative Activity of Substituted β-Carbolines

Substituted β-carbolines were tested for antiproliferative activity against HCT116 colon cancer cells and HPAC, Mia-PaCa2 and Panc-1 pancreatic cell lines. Table 1 lists the IC50 values for the substituted β-carbolines. Compounds 11, 19, 25, 29, 30, and 36 demonstrated significantly lower IC50 values.

TABLE 1

| Cmpd | HCT116 IC50 (μM) | HCT116 P53 −/− IC50 (μM) | HPAC IC50 (μM) | Mia-PaCa2 IC50 (μM) | Panc-1 IC50 (μM) |
| --- | --- | --- | --- | --- | --- |
| 84 | — | | 21.64 | 12.52 | >50.00 |
| 5 | — | | >50.00 | 44.83 | >50.00 |
| 10 | 7.00 | 18.7 | | | |
| 11 | 0.51 | 0.46 | 0.56 | 0.49 | 0.58 |
| 8 | — | | 45.11 | 38.28 | >50.00 |
| 9 | 60.90 | 53.7 | 45.1 | | |
| 12 | — | | 34.77 | 49.17 | >50.00 |
| 125 | — | | 5.14 | 13.42 | 9.30 |
| 13 | 26.10 | | >50.00 | >50.00 | >50.00 |
| 14 | 49.60 | | >50.00 | >50.00 | >50.00 |
| 15 | 5.70 | | 7.37 | 4.70 | 10.46 |
| 16 | 33.50 | | 44.88 | 36.73 | >50.00 |
| 17 | 14.10 | | 21.88 | 17.02 | 28.96 |
| 18 | 13.10 | | 14.45 | 16.72 | 37.21 |
| 19 | 0.13 | | 0.29 | 0.20 | 0.29 |
| 20 | 3.60 | | 25.54 | 6.61 | >50.00 |
| 21 | 0.90 | | 5.83 | 2.58 | 7.52 |
| 22 | 12.80 | | >50.00 | 28.55 | >50.00 |
| 23 | 9.00 | | 15.92 | 9.81 | 21.20 |
| 24 | 15.10 | | 34.40 | 24.06 | >50.00 |
| 25 | 0.67 | | 5.57 | 1.36 | 8.40 |
| 26 | 17.10 | | 20.76 | 21.68 | 48.03 |
| 27 | 2.10 | | 6.08 | 2.43 | 10.49 |
| 28 | 1.70 | | 5.47 | 3.59 | 14.94 |
| 29 | 0.53 | | 0.54 | 0.84 | 17.97 |
| 30 | 0.87 | | 5.67 | 1.57 | >50.00 |
| 31 | 33.50 | | 44.79 | 37.05 | >50.00 |
| 32 | 31.40 | | 34.27 | 34.30 | >50.00 |
| 33 | 1.80 | | 9.38 | 2.23 | 19.76 |
| 34 | 2.43 | | 17.63 | 20.74 | 33.28 |
| 35 | 2.22 | | 23.12 | 47.19 | >50.00 |
| 36 | — | | 0.83 | 0.51 | 0.57 |
| 37 | 2.60 | | 6.39 | 3.54 | >50.00 |
| 38 | 3.00 | | 17.03 | 48.40 | 47.35 |

Figure 1B:
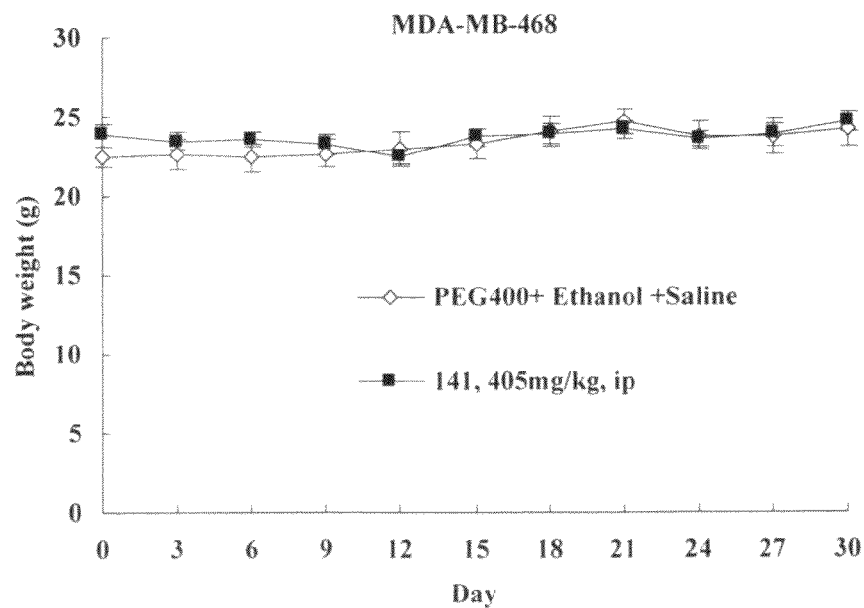
Figure 2A:
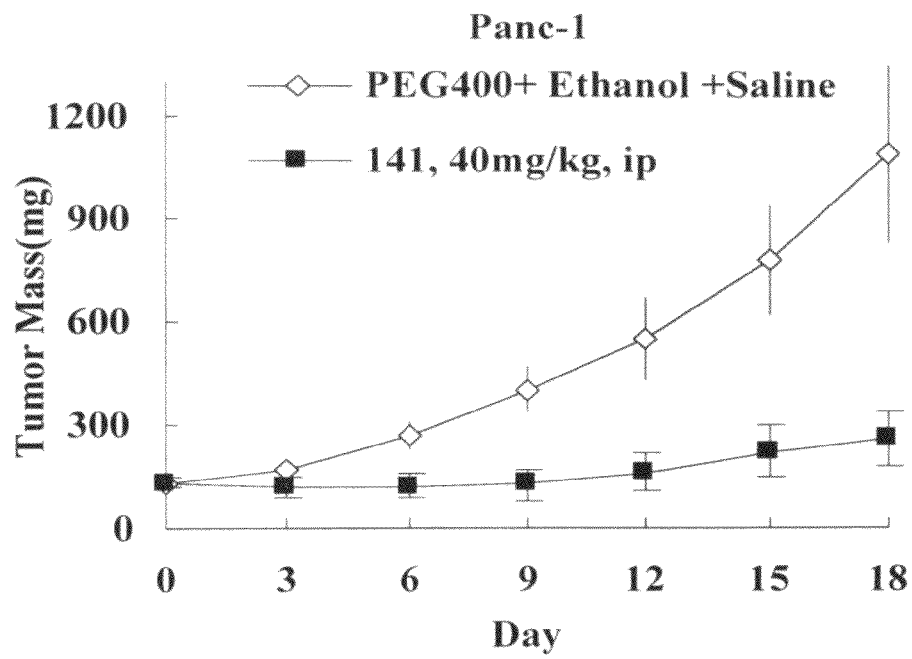
FIGS. 2A-2B illustrate antitumor activity on tumor mass (FIG. 2A) and on body weight (FIG. 2B) of compound 19 treatment in nude mice bearing Panc-1 human pancreatic cancer xenografts.
Figure 2B:
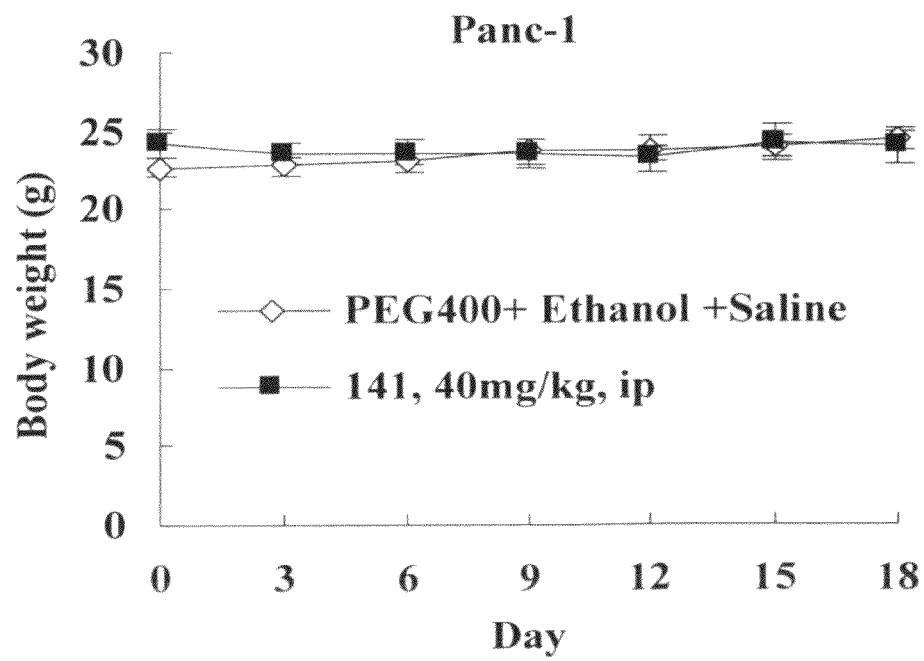

Nude mice bearing MDA-MB-468 breast cancer (FIGS. 1A-1B) and Panc-1 pancreatic cancer (FIGS. 2A-2B) xenografts were administered 40 mg/kg i.p. of compound 19 and tumor mass and body weights were measured daily for 18 days compared to a PEG-ethanol-saline control. After 18 days the tumor mass had not increased nor had body weight decreased in these mice.

Figure 3A:
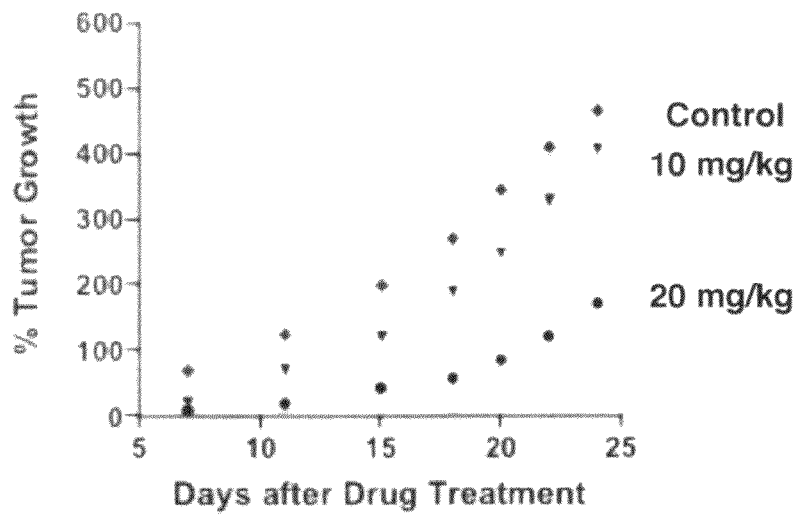
FIGS. 3A-3B illustrate antitumor activity on tumor growth (FIG. 3A) and on body weight (FIG. 3B) of compound 19 treatment in nude mice bearing human DUI145 prostate cancer xenografts.
Figure 3B:
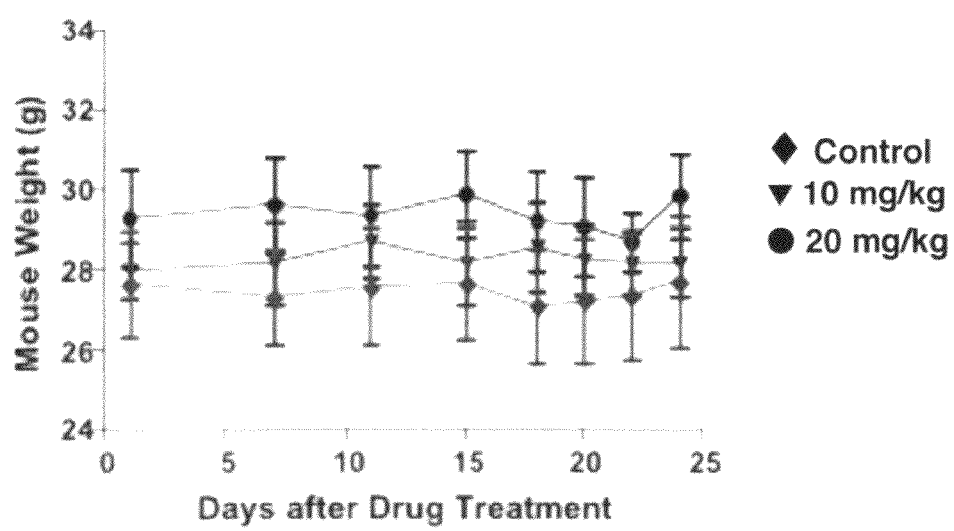

Nude mice bearing DU145 prostate cancer xenografts were administered i.p. 10 mg/kg, 20 mg/kg or control of compound 19 and tumor growth (FIG. 3A) and body weight (FIG. 3B) was monitored over 25 days. Although the percent of tumor growth at about day 7 in the presence of 10 mg/kg cmpd. 19 was less than control and substantially the same as with a dose of 20 mg/kg, the rate of tumor growth over the 25 days was about equivalent to that of control. A dose of 20 mg/kg showed significant decrease in tumor growth compared to 10 mg/kg and control. Body weights remained fairly constant for each dosing level although the average body weight for 20 mg/kg>10 mg/kg>control over the 25 days.

EXAMPLE 3

β-carboline Induced Apoptosis

Flow cytometry experiments were performed to show the effects of Compound 19, and anticancer drugs Adriamycin or Camptothecin treatment on the cell cycle kinetics of various human cells (FIGS. 7A-7I and 8A-8I), MCF-7 breast cancer cells (FIGS. 4A-4F), A549 lung cancer cells (FIGS. 6A-6I), LNCaP (FIGS. 9A-9I), DU145 (FIGS. 10A-10I) and PC-3 (FIGS. 11A-11I) prostate cancer cells, as well as cultured normal human fibroblasts (FIGS. 5A-5F). The compound or drugs were applied at a concentration of 15 mM in 0.1% DMSO as the vehicle, and cells incubated for the time point indicated in hours (hr). The control samples were treated with vehicle without compound or drug. Red histograms represent cells in the G1/G0 phase (histogram to the left) and cells in the G2/M phases (histogram to the right). The interval between the G1/G) and G2/M histograms is the S-phase of the cell cycle. The subG1/GO histograms (cyan colored) represent cells undergoing apoptosis (programmed cell death).

Adriamycin and Camptothecin were included to show that the mechanism of anticancer activity of compound 19 differed from those of these conventional anticancer drugs. Thus, whereas Adriamycin and Camptothecin kill cancer cells by a mechanism(s) involving primarily G1 phase arrest, compound 19 on the other hand kills cancer cells by a G2/M arrest mechanism(s). This also will make combination therapy of compound 19 with these drugs rationale since one will be targeting multiple mechanisms of cancer cell destruction. Also, the results with the normal human fibroblast cells show that Compound 19 has no significant perturbation of the cell cycle of normal human cells implying that it will be a selective anticancer agent that will mainly destroy cancer cells while sparing normal cells, a very attractive property for a cancer drug. This is unlike the conventional chemotherapy drugs Adriamycin and Camptothecin which did not show selectivity between the cancer cells and the normal (fibroblast) cells and perturbed their cell cycle kinetics equally well.

The following references are cited herein.

1. Cao et al. Current Medicinal Chemistry 14:479-500 (2007).
2. Song et al. Bioorganic & Medicinal Chemistry Letters 12:1129-1132.
3. Sunder-Plassman et al. Bioorg. Med. Chem. 13:6094-6111.
4. Liu et al. Biochem. Pharmacol. 70:287-299.
5. Frédérich et al. J Pharmacol Exp Ther, 304(3):1103-1110 (2003).

Any patents or publications mentioned in this specification are indicative of the levels of those skilled in the art to which the invention pertains. These patents and publications are incorporated by reference herein to the same extent as if each individual publication was incorporated by reference specifically and individually. One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A β-carboline compound having the structure:

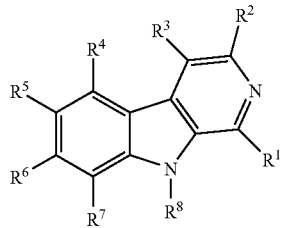

wherein $R^1$ is furanyl, 1-naphthyl, anthracyl, phenanthracyl, 3-quinolinyl, 5-quinolinyl, isoquinolinyl, quinoxalinyl, phenyl substituted with pyridinyl each optionally substituted with $C_1$-$C_4$ alkyl or $C_1$-$C_4$ alkoxy; and $R^2$, $R^3$, $R^4$, $R^5$, $R^6$, $R^7$, and $R^8$ are independently —H, $C_1$-$C_4$ alkyl, $C_1$-$C_4$ alkoxy, or $C_1$-$C_4$ alkoxyphenyl; wherein one of $R^5$, $R^6$ or $R^7$ is $C_1$-$C_4$ alkoxy or $C_1$-$C_4$ alkoxyphenyl.

2. The β-carboline compound of claim 1, wherein $R^1$ is 3-furanyl, 3-quinolinyl, 5-quinolinyl, 1-isoquinolinyl, 4-isoquinolinyl, 5-isoquinolinyl, 5-quinoxalinyl, 6-quinoxalinyl, 1-naphthyl, 2-methyl-1-naphthyl, 6-methoxy-1-naphthyl, 9-anthracyl, 9-phenanthracyl, 4-pyridin-2-yl-phenyl, or a group with the structure:

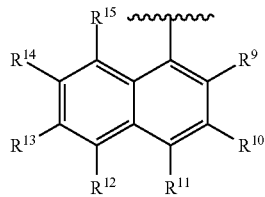

wherein $R^9$, $R^{10}$, $R^{11}$, $R^{12}$, $R^{13}$, $R^{14}$, and $R^{15}$ are independently $C_1$-$C_4$ alkyl or $C_1$-$C_4$ alkoxy;

$R^2$, $R^3$, and $R^4$ are H;

$R^5$ is —$OCH_3$, —$OCH_2$(phenyl), or H;

$R^6$ is —$OCH_3$ or H;

$R^7$ is —$CH_3$ or H;

$R^8$ is H; and wherein (1) $R^5$ is —$OCH_3$ or —$OCH_2$(phenyl) when $R^6$ is H, or (2) $R^5$ is —H when $R^6$ is —$OCH_3$.

3. The β-carboline compound of claim 2, wherein $R^1$ is 3-furanyl, 3-quinolinyl, 5-quinolinyl, 4-isoquinolinyl, 5-isoquinolinyl, 5-quinoxalinyl, 6-quinoxalinyl, 1-naphthyl, 2-methyl-1-naphthyl, 6-methoxy-1-naphthyl, 9-anthracyl, 9-phenanthracyl, or 4-pyridin-2-yl-phenyl; $R^5$ is —$OCH_3$; $R^6$ is H; and $R^7$ is H.

4. The β-carboline compound of claim 2, wherein $R^1$ is 3-furanyl, 3-quinolinyl, 5-quinolinyl, 1-isoquinolinyl, 4-isoquinolinyl, 5-isoquinolinyl, 5-quinoxalinyl, 6-quinoxalinyl, 1-naphthyl, 2-methyl-1-naphthyl, 9-anthracyl, or 9-phenanthracyl; $R^6$ is —$OCH_3$; $R^5$ is H; and $R^7$ is H.

5. The β-carboline compound of claim 2, wherein $R^1$ is 1-naphthyl; $R^5$ is —$OCH_2$(phenyl); $R^6$ is H; and $R^7$ is —H.

6. A pharmaceutical composition comprising the β-carboline compound of claim 1 and a pharmaceutically effective carrier.

7. A β-carboline compound selected from the group consisting of
1-furan-3-yl-6-methoxy-9H-β-carboline,
1-furan-3-yl-7-methoxy-9H-β-carboline,
1-lsoquinolin-1-yl-7-methoxy-9H-β-carboline,
6-methoxy-1-quinoxalin-5-yl-9H-β-carboline,
7-methoxy-1-quinoxalin-5-yl-9H-β-carboline,
6-methoxy-1-quinoxalin-6-yl-9H-β-carboline,
7-methoxy-1-quinoxalin-6-yl-9H-β-carboline,
1-isoquinolin-4-yl-6-methoxy-9H-β-carboline,
1-isoquinolin-4-yl-7-methoxy-9H-β-carboline,
6-methoxy-1-quinolin-3-yl-9H-β-carboline,
7-methoxy-1-quinolin-3-yl-9H-β-carboline,
6-methoxy-1-naphthalen-1-yl-9H-β-carboline,
7-methoxy-1-naphthalen-1-yl-9H-β-carboline,
6-methoxy-1-quinolin-5-yl-9H-β-carboline,
7-methoxy-1-quinolin-5-yl-9H-β-carboline,
1-isoquinolin-5-yl-6-methoxy-9H-β-carboline,
1-isoquinolin-5-yl-7-methoxy-9H-β-carboline,
1-anthrac-9-yl-6-methoxy-9H-β-carboline,
1-anthrac-9-yl-7-methoxy-9H-β-carboline,
6-methoxy-1-phenanthrac-9-yl-9H-β-carboline,
7-methoxy-1-phenanthrac-9-yl-9H-β-carboline,
7-methoxy-1-phenyl-9H-β-carboline,
6-methoxy-1-(2-methyl-naphthalen-1-yl)-9H-β-carboline,
7-methoxy-1-(2-methyl-naphthalen-1-yl)-9H-β-carboline,
6-methoxy-1-(6-methoxy-naphthalen-1-yl)-9H-β-carboline,
6-benzyloxy-1-naphthalen-1-yl-9H-β-carboline, and
6-methoxy-1-(4-pyridin-2-yl-phenyl)-9H-β-carboline.

* * * * *